(12) United States Patent
Lee

(10) Patent No.: US 11,185,620 B2
(45) Date of Patent: Nov. 30, 2021

(54) FLUID PUMPING DEVICE AND BLOOD PURIFYING APPARATUS HAVING THE SAME

(71) Applicant: Jake K Lee, South Burlington, VT (US)

(72) Inventor: Jake K Lee, South Burlington, VT (US)

(73) Assignee: Exorenal Inc., Baltimore, MD (US)

(*) Notice: Subject to any disclaimer, the term of this patent is extended or adjusted under 35 U.S.C. 154(b) by 336 days.

(21) Appl. No.: 16/573,934

(22) Filed: Sep. 17, 2019

(65) Prior Publication Data

US 2020/0086031 A1 Mar. 19, 2020

Related U.S. Application Data

(60) Provisional application No. 62/731,998, filed on Sep. 17, 2018, provisional application No. 62/889,379, filed on Aug. 20, 2019.

(30) Foreign Application Priority Data

Sep. 17, 2019 (KR) .................... 10-2019-0114095

(51) Int. Cl.
*A61M 1/30* (2006.01)
*A61M 1/16* (2006.01)
*A61M 1/34* (2006.01)

(52) U.S. Cl.
CPC ........ *A61M 1/1645* (2014.02); *A61M 1/1635* (2014.02); *A61M 1/306* (2014.02); *A61M 1/1649* (2014.02); *A61M 1/308* (2014.02); *A61M 1/3427* (2014.02); *A61M 2202/0413* (2013.01); *A61M 2205/103* (2013.01); *A61M 2205/3334* (2013.01); *A61M 2205/75* (2013.01)

(58) Field of Classification Search
CPC ........ A61M 1/30; A61M 1/301; A61M 1/306; A61M 1/14; A61M 1/16; A61M 1/1601; A61M 1/1645; A61M 1/1647; A61M 1/1649; A61M 1/165; A61M 1/1694; A61M 2205/0413; A61M 2205/103; A61M 2205/3334; A61M 2205/75
See application file for complete search history.

(56) References Cited

U.S. PATENT DOCUMENTS

| | | | |
|---|---|---|---|
| 6,979,309 B2 * | 12/2005 | Burbank | A61M 1/282 604/6.16 |
| 2005/0131332 A1 * | 6/2005 | Kelly | A61M 1/1613 604/4.01 |
| 2016/0151554 A1 * | 6/2016 | Jansson | G05B 15/02 210/646 |

* cited by examiner

*Primary Examiner* — Philip R Wiest
(74) *Attorney, Agent, or Firm* — Jake K. Lee

(57) ABSTRACT

Provided is a blood purifying apparatus including a blood purifying filter in which mass transfer occurs between blood and dialysis fluid, a blood tube connecting the blood purifying filter and a patient to allow blood to flow therethrough, a dialysis fluid supply tube connected to the blood purifying filter and allowing dialysis fluid to be supplied to the blood purifying filter therethrough, a dialysis fluid discharge tube connected to the blood purifying filter and allowing dialysis fluid to be discharged from the blood purifying filter therethrough; and a fluid pumping device. The fluid pumping device further includes a plurality of chamber each having an internal space, a chamber pressurizing member disposed inside the plurality of chambers and compressing or expanding the chambers to thereby allow a fluid to flow therethrough, and a flow controller controlling a flow passage.

17 Claims, 32 Drawing Sheets

FIG. 8
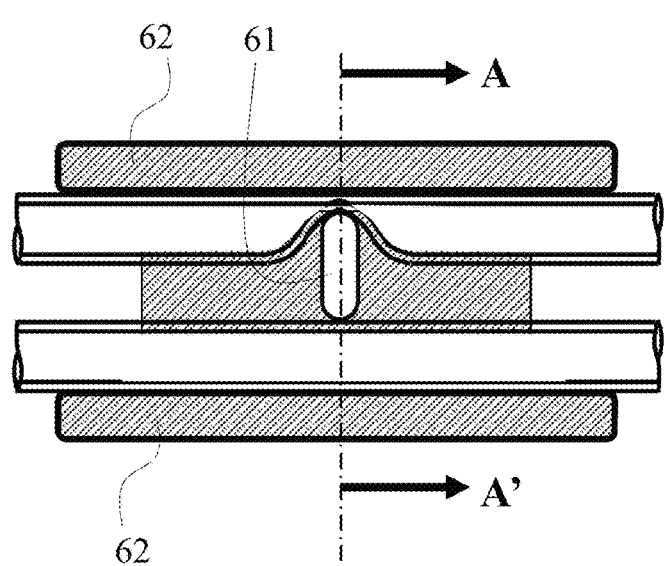
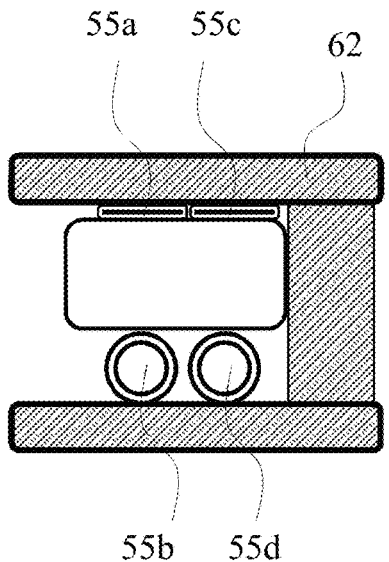
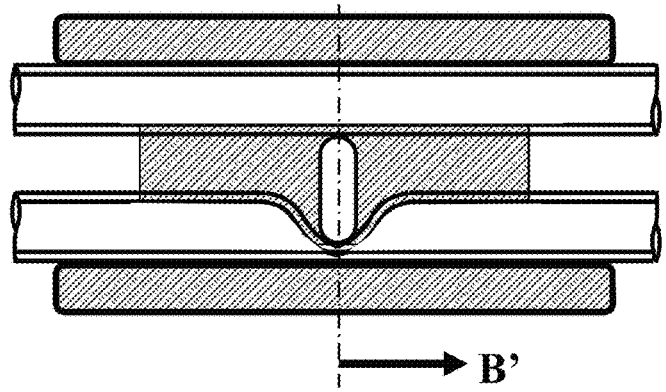
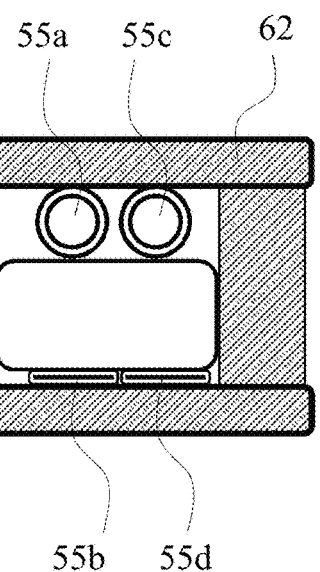

FIG. 9
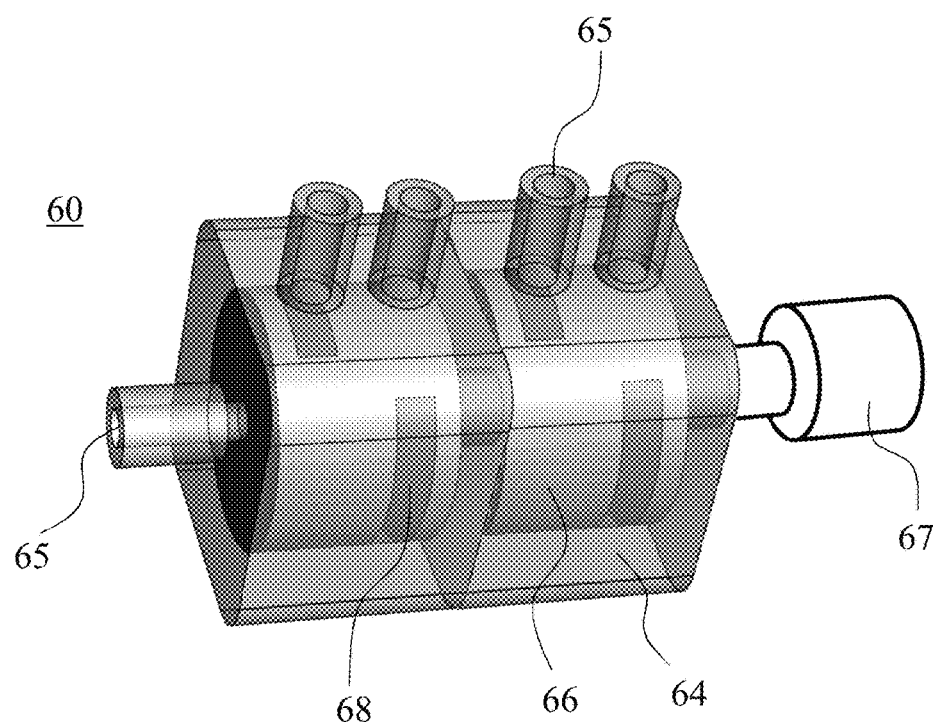
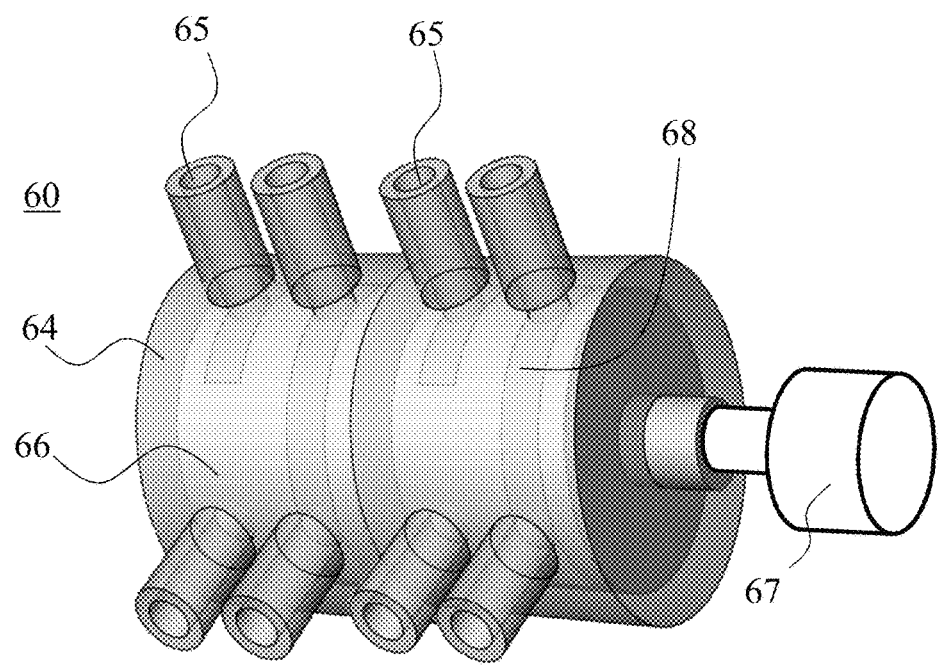

"Compression Phase"

"Expansion Phase"
(e.g., for 5 seconds)

"Compression Phase" (e.g., for 5 seconds)

FIG. 30
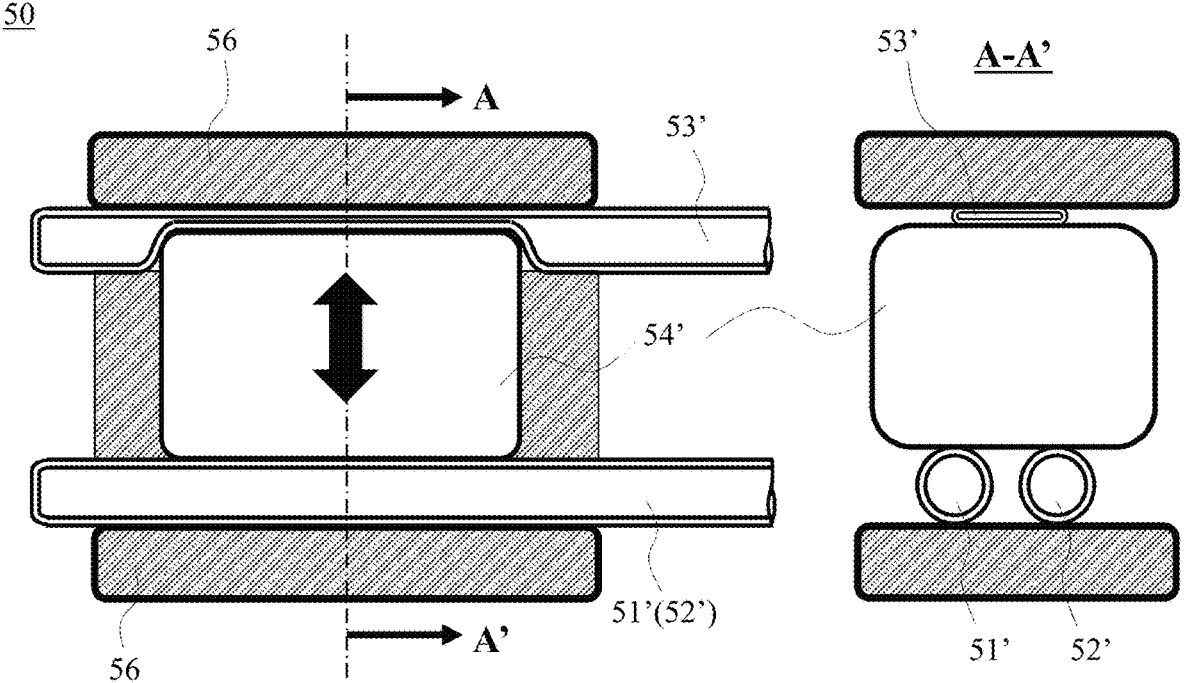
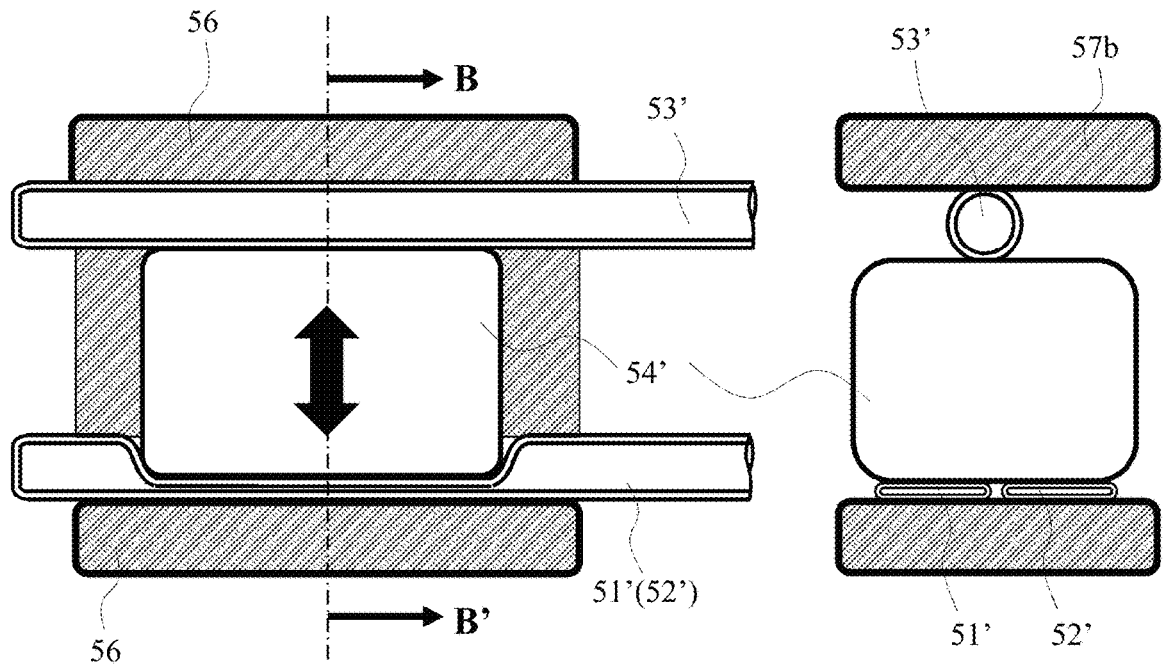

FLUID PUMPING DEVICE AND BLOOD PURIFYING APPARATUS HAVING THE SAME

CROSS-REFERENCE TO RELATED APPLICATIONS

This application claims the benefit of priority to U.S. Provisional Patent Application Ser. Nos. 62/731,998 filed on Sep. 17, 2018 and 62/889,379 filed on Aug. 20, 2019, and claims priority under 35 U.S.C. § 119 to Korean Patent Application No. 10-2019-0114095 filed on Sep. 17, 2019, the entire contents of which are incorporated by reference herein.

TECHNICAL FIELD

The present invention is related to a fluid pumping device and a blood purifying apparatus having the same to purify blood of a patient, and more particularly, to a fluid pumping device including multiple chambers and a chamber pressurizing member to enhance convective mass transfer and increase blood purifying efficiency without deteriorating a diffusive mass transfer between blood and dialysis fluid and the blood purifying apparatus having the same.

BACKGROUND

The present invention relates to a blood purifying apparatus configured to improve water exchange and mass transfer between blood and dialysis fluid by quickly changing the dialysis fluid pressure in a blood purifying filter using a pulsatile dialysis fluid flow.

When there is a kidney dysfunction, water and waste products that have to be discharged out of body accumulate in blood and imbalance of electrolytes in the body occurs. Most commonly performed to improve such a kidney failure symptom, is hemodialysis which is to circulate blood out of body and rid the blood of the accumulated uremic toxin and excess water by a semi-permeable dialysis membrane. Hemodialysis is a method of seeking an electrolyte balance and ridding the body fluid of uremic toxin and excess water, taking advantages of diffusion applied due to the concentration difference and filtration applied due to the pressure difference between blood and dialysis fluid.

Most commonly used of blood purifying filter is the type that is a chamber-shape container charged with a bundle of hollow fiber membranes and port-processed at both ends thereof by use of a synthetic resin like polyurethane. It is because the hollow fiber blood purifying filter has excellent mass-transfer efficiency resulting from large effective surface area between blood and dialysis fluid compared to the small size as a whole.

A blood purifying apparatus includes a blood purifying filter in which mass transfer occurs between blood and dialysis fluid, a blood pump designed to circulate a patient's blood, a dialysis fluid pump that supplies or discharges dialysis fluid. Blood and dialysis fluid each decrease their hydraulic pressure while passing through a blood purifying filter. Since blood and dialysis fluid flow in opposite directions inside the blood purifying filter, a filtration occurs at the proximal part of the blood purifying filter such that water in the blood moves toward dialysis fluid compartment because blood pressure is higher than dialysis fluid pressure, while a backfiltration occurs at the distal part such that water in the dialysis fluid moves toward blood domain for the same reason.

When a filtration takes place, wastes in blood are also eliminated, which is referred to as a convective mass transfer. It is known that uremic toxins of medium molecular size are efficiently removed by the convective mass transfer and thus dialysis efficiency and prognosis on patients have greatly improved. However, there is a big hurdle in the effort to improve dialysis efficiency by the convective mass transfer, because blood purifying filters in typical blood purifying apparatuses are limited in size and blood flow rate is restrictively allowed to be increased in consideration of the weight and blood vessel condition of a patient.

SUMMARY

The present invention provides a blood purifying apparatus, which include a blood purifying filter in which mass transfer occurs between blood and dialysis fluid, a blood tube connecting between a patient and the blood purifying filter to allow blood of a patient to flow therethrough, a blood pump disposed in the blood tube to transfer blood, a dialysis fluid supply tube through which dialysis fluid is supplied to the blood purifying filter, a dialysis fluid discharge tube through which dialysis fluid of the blood purifying filter is discharged therefrom, a first dialysis fluid pump disposed on the dialysis fluid supply tube to supply dialysis fluid to the blood purifying filter, and a second dialysis fluid pump disposed on the dialysis fluid discharge tube to discharge the used dialysis fluid from the blood purifying filter.

In addition, the blood purifying apparatus may be additionally provided with a fluid pumping device which is capable of enhancing the total volume of filtration during the blood purification treatment. The fluid pumping device may include a plurality of fluid chamber each having an internal space, such as a first chamber, a second chamber, and a third chamber. The fluid pumping device may also include a chamber pressurizing member which compresses or expands the internal spaces of the chambers so as to allow a fluid to flow through the chambers. Here, the fluid pumping device may be provided with separate chamber pressurizing members for each of the chambers, such as a first chamber pressurizing member, a second chamber pressurizing member, and a third chamber pressurizing member. However, the chamber pressurizing member may compress or expand the internal spaces of the chambers at the same time (such as compressing a portion of the chambers while expanding the other portion of the chambers), and it may operate using a single chamber pressurizing member driver.

The chambers may have a cylindrical shape and a piston-shaped chamber pressurizing member may be disposed inside the chambers. The chamber pressurizing member driver (now shown) allows the chamber pressurizing member to reciprocate along a straight line to compress or expand the internal spaces of the chambers. As aforementioned, since the chamber pressurizing member compresses or expands the chamber simultaneously, a single chamber pressurizing member driver may be used to drive the chamber pressurizing member.

Here, the first chamber may be connected to the first supply tube and the second supply tube. Specifically, the first chamber may be connected to the first supply tube and the downstream second supply tube when the balancing chamber is provided. In a similar manner, the second chamber may be connected to the first discharge tube and the second discharge tube. Specifically, the second chamber may be connected to the first discharge tube and the downstream second discharge tube when the balancing chamber is provided.

In addition, a first chamber tube and a second chamber tube may be provided for the connection between the first chamber and the dialysis fluid supply tube. In addition, third chamber tube and a fourth chamber tube may be provided for the connection between the second chamber and the dialysis fluid discharge tube. The first chamber may be connected to the first supply tube through the first chamber tube where a fluid is supplied to the first chamber and to the downstream second supply tube through the second chamber tube where a fluid is discharged from the first chamber. Likewise, the second chamber may be connected to the first discharge tube through the third chamber tube where a fluid is supplied to the second chamber and to the downstream second discharge tube through the fourth chamber tube where a fluid is discharged from the second chamber.

The third chamber may be connected with the fifth chamber tube through with a fluid is supplied to or discharged from the third chamber. Specifically, the third chamber may be connected to the second blood tube through the fifth chamber tube.

The fluid pumping device may further include a flow controller which regulates flow passages through the first chamber tube, the second chamber tube, the third chamber tube, and the fourth chamber tube. The flow controller controls the inflow and outflow through the first chamber and the second chamber.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 8 to 10 are views illustrating a flow controller of a fluid pumping device according to an embodiment of the present invention;

FIG. 30 is a view illustrating a fluid pumping device according to another embodiment of the present invention;

DETAILED DESCRIPTION OF PREFERRED EMBODIMENTS

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

As used herein, the singular forms "a," "an," and "the" are intended to include the plural forms as well, unless the context clearly indicates otherwise. It will be understood that when an element or layer is referred to as being "on," "connected to," "coupled to," or "adjacent to" another element or layer, it can be directly on, connected, coupled, or adjacent to the other element or layer, or intervening elements or layers may be present. The same reference denotations may be used to refer to the same or substantially the same elements throughout the specification and the drawings.

Hereinafter, a blood purifying apparatus according to embodiments of the present invention will be described in detail with reference to the accompanying drawings.

Figure 1:
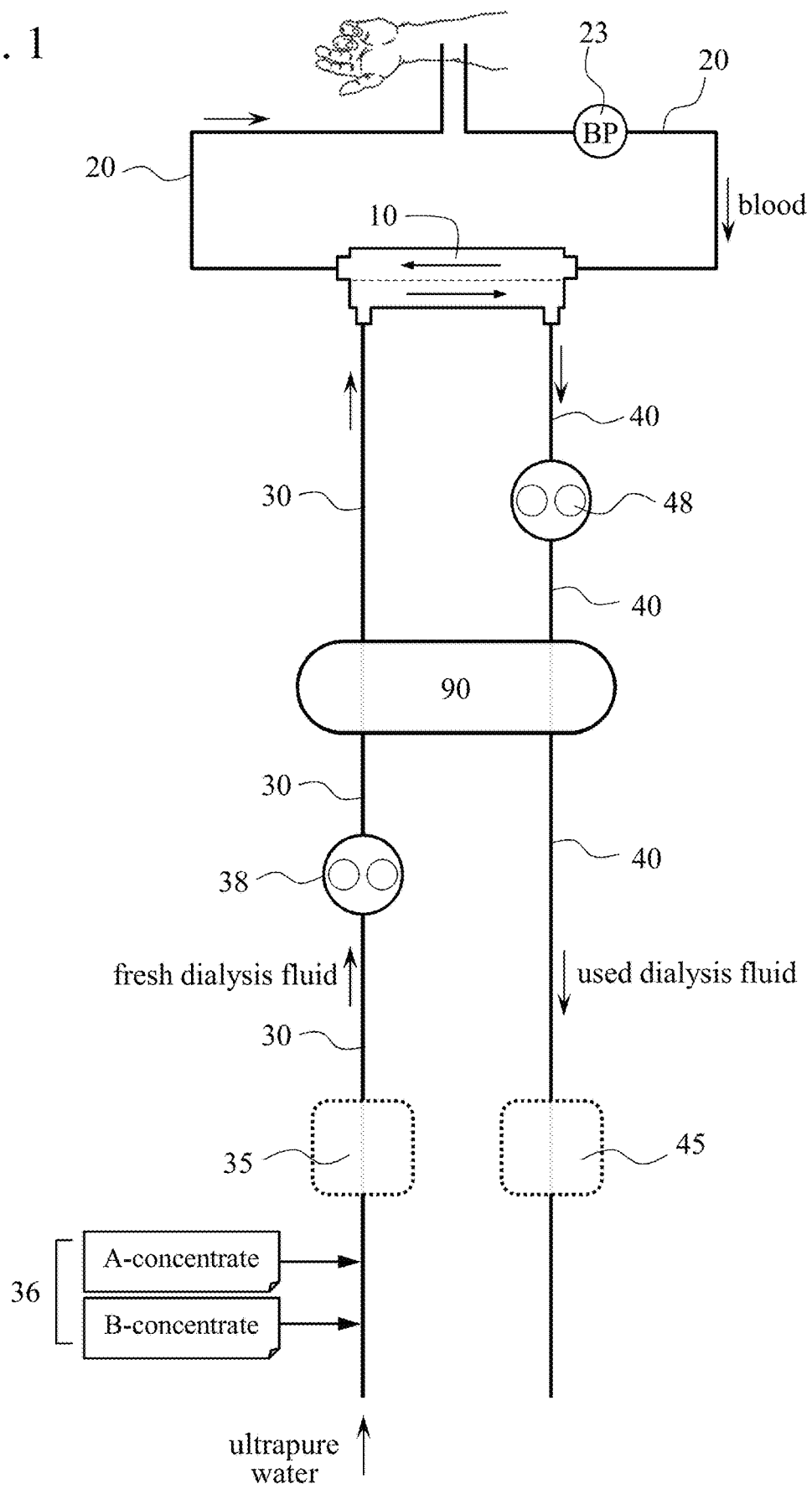
FIGS. 1 and 2 are views illustrating a blood purifying apparatus according to an embodiment of the present invention.
Figure 2:
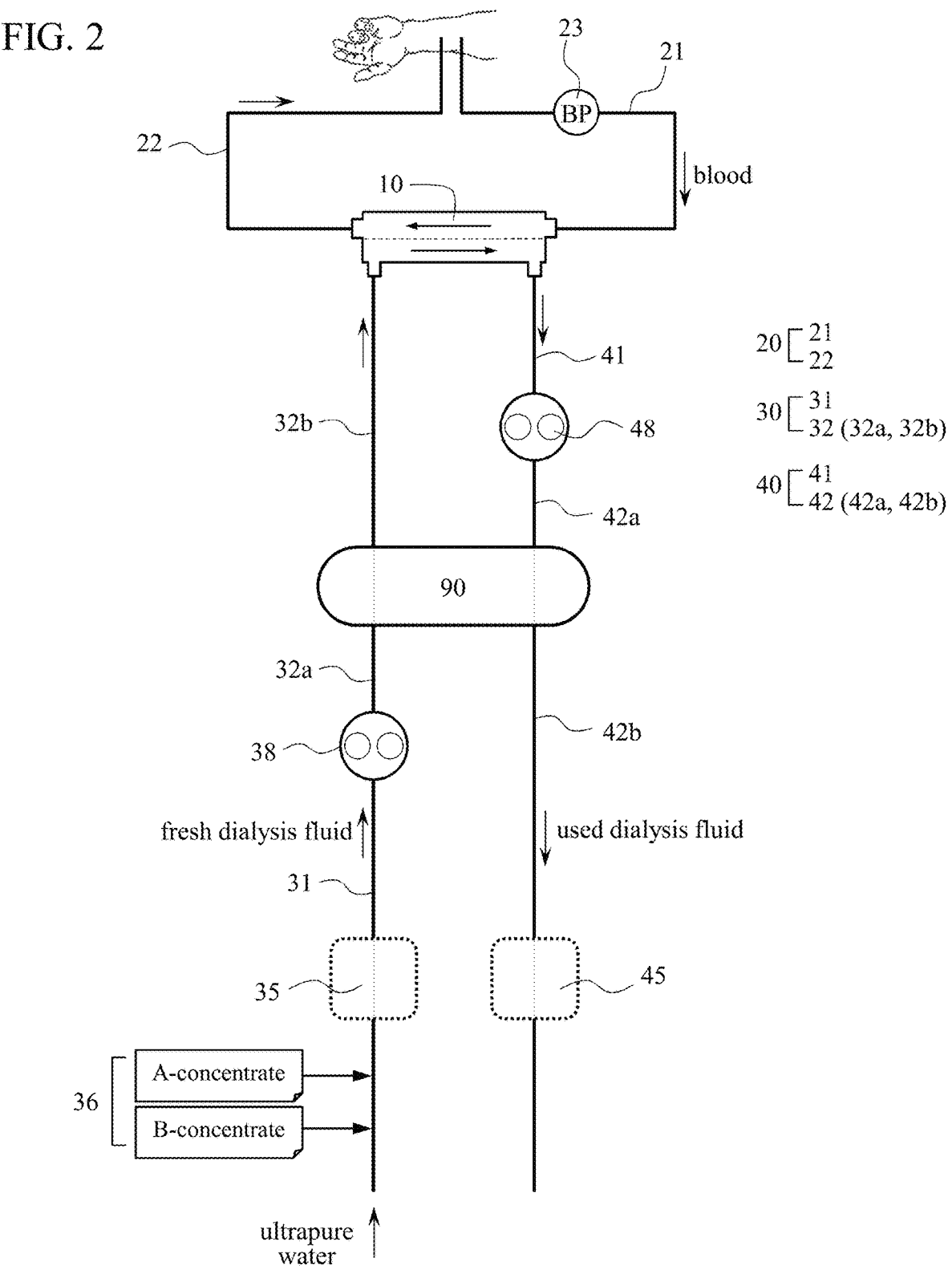

FIGS. 1 and 2 are schematic diagrams of a blood purifying apparatus according to an embodiment of the present invention. The blood purifying apparatus 1 shown in FIGS. 1 and 2 are the device for hemodialysis to treat patients with end-stage renal disease (ESRD). However, the blood purifying apparatus 1 according to an embodiment of the present invention is not limited to the hemodialysis device, and may include a device for liver dialysis for patients with acute or acute-on-chronic liver failure, a device for treating patients with multiple organ failure, or a device for treating patients requiring detoxification. The blood purifying apparatus 1 includes the devices for replacing impaired functions of an organ including a lung, a kidney, a liver, or a heart.

As shown in FIGS. 1 and 2, the blood purifying apparatus 1 according to an embodiment of the present invention may include a blood purifying filter 10 in which mass transfer occurs between blood and dialysis fluid, a blood tube 20 connecting between a patient and the blood purifying filter 10 to allow blood of a patient to flow therethrough, a blood pump 23 disposed in the blood tube 20 to transfer blood, a dialysis fluid supply tube 30 through which dialysis fluid is supplied to the blood purifying filter 10, a dialysis fluid discharge tube 40 through which dialysis fluid of the blood purifying filter 10 is discharged therefrom, a first dialysis fluid pump 38 disposed on the dialysis fluid supply tube 30 to supply dialysis fluid to the blood purifying filter 10, and a second dialysis fluid pump 48 disposed on the dialysis fluid discharge tube 40 to discharge the used dialysis fluid from the blood purifying filter 10.

As shown in FIG. 2, the blood tube 20 may further include a first blood tube 21 and a second blood tube 22. Blood of a patient is supplied to the blood purifying filter 10 through the first blood tube 21 and blood having passed through the blood purifying filter 10 is returned to a patient through the second blood tube 22 which connects the blood purifying filter 10 and a patient.

The dialysis fluid supply tube 30 may also include a first supply tube 31 through which dialysis fluid is supplied to the first dialysis fluid pump 38 and a second supply tube 32 connecting the first dialysis fluid pump 38 and the blood purifying filter 10 and through which dialysis fluid is supplied to the blood purifying filter 10.

Similarly, the dialysis fluid discharge tube 40 may include a first discharge tube 41 connecting the blood purifying filter 10 and the second dialysis fluid pump 48 and allowing the dialysis fluid of the blood purifying filter to flow to the second dialysis fluid pump 48 and a second discharge tube 42 through which dialysis fluid is discarded from the second dialysis fluid pump 48.

The blood purifying apparatus 1 may further include a balancing chamber 90 which severs as a means of keeping the amount of the dialysis fluid supplied to the blood purifying filter 10 substantially equal to the amount of the dialysis fluid discharged from the blood purifying filter 10. In an embodiment, the balancing chamber 90 may be able to allow the dialysis fluid amount flowing by the first dialysis fluid pump 38 to be substantially same as the dialysis fluid amount flowing by the second dialysis fluid pump 48. The balancing chamber 90 may use various methods such as a volumetric ultrafiltration (UF) control unit to enable the dialysis fluid to flow at the same rate upstream and downstream of the blood purifying filter 10.

When the balancing chamber 90 is provided, the second supply tube 32 may further be divided into an upstream second supply tube 32a connecting the first dialysis fluid pump 38 and the balancing chamber 90, and a downstream second supply tube 32b connecting the balancing chamber 90 and the blood purifying filter 10. Similarly, when the balancing chamber 90 is provided, the second discharge tube 42 may further include an upstream second discharge tube 42a connecting the second dialysis fluid pump 48 and the balancing chamber 90 and a downstream second discharge tube 42b through which used dialysis fluid is discarded from the balancing chamber 90.

The blood purifying apparatus 1 according to an embodiment of the present invention may include a dialysis fluid processing unit 36 which makes the dialysis fluid for the blood purifying treatment. For example, the dialysis fluid processing unit 36 may adjust ion and/or bicarbonate concentrations of the dialysis fluid within a predetermined level or at a desired range. The dialysis fluid processing unit 36 may be provided near or in the first supply tube 31 to make the fresh dialysis fluid ready for the blood purifying treatments.

The fresh dialysis fluid according to an embodiment of the present invention may be made by adding acid and/or bicarbonate solutions (or acid and/or bicarbonate powder) to ultrapure water which is prepared through a water treatment unit. However, the fresh dialysis fluid may be prepared in other ways such as using a pre-made dialysis fluid bag.

The blood purifying apparatus 1 according to an embodiment of the present invention can include a fresh dialysis fluid reservoir 35 to store fresh dialysis fluid and a used dialysis fluid reservoir 45 in which used dialysis fluid is collected. However, fresh dialysis fluid may be supplied to the blood purifying filter 10 without being stored in the fresh dialysis fluid reservoir 35, and used dialysis fluid may be discarded without being collected in the used dialysis fluid reservoir 45.

Figure 3:
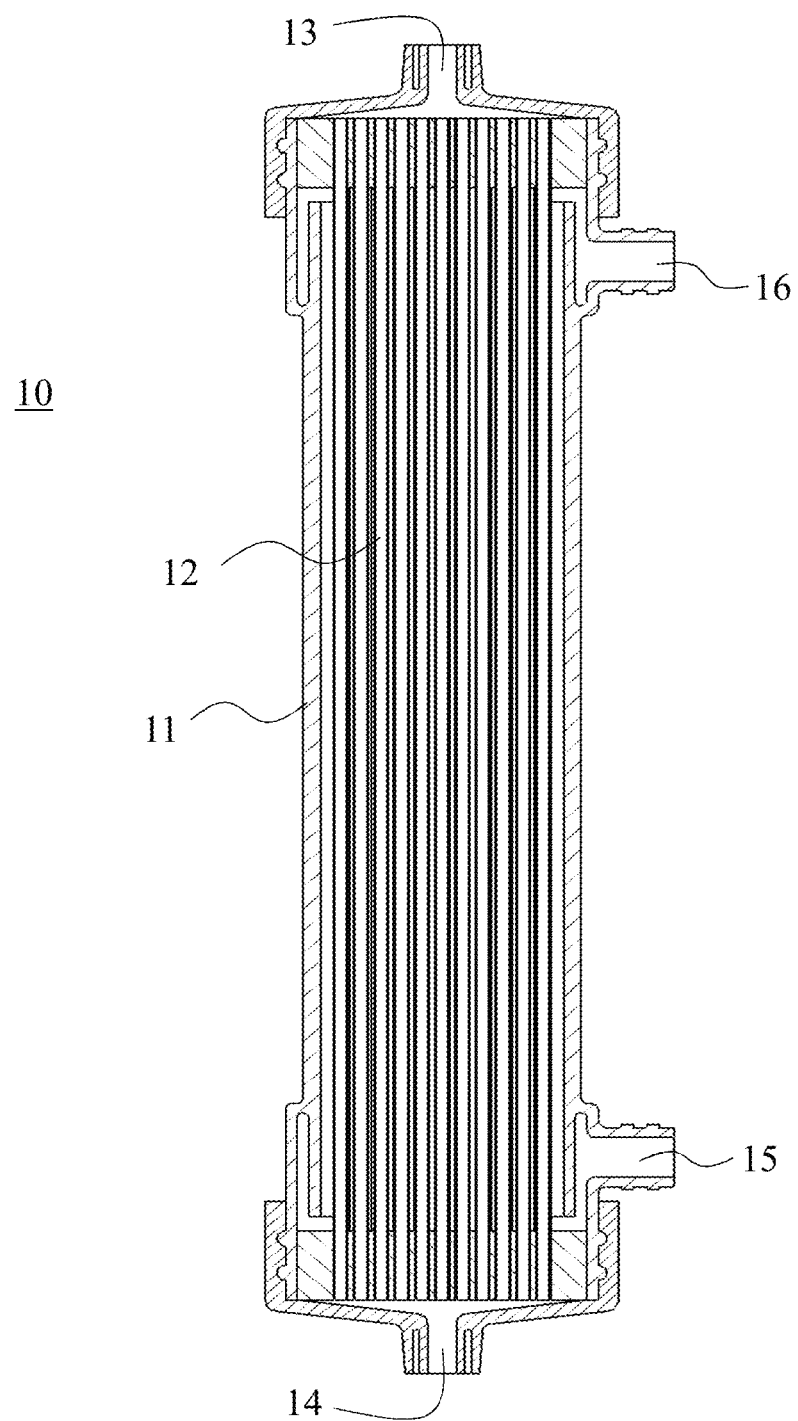
FIG. 3 is a view illustrating a blood purifying filter according to an embodiment of the present invention.

The blood purifying filter 10 may include various filter apparatuses to purify blood. FIG. 3 illustrates an exemplary blood purifying filter 10. The blood purifying filter 10 may include a blood purifying filter container 11 having an internal space and a blood purifying membrane 12 accommodated in the internal space of the blood purifying filter container 11. The internal space of the blood purifying filter container 11 may be divided into a blood flow region and a dialysis fluid flow region by the blood purifying membrane 12. The blood purifying filter container 11 includes a blood inlet 13 disposed at one end thereof and a blood outlet 14 disposed at the other end thereof. Also, a dialysis fluid inlet 15 and a dialysis fluid outlet 16 may be provided on the outer surface of the blood purifying filter container 11. Blood passes through the blood flow region inside the blood purifying filter 10 and dialysis fluid passes through the dialysis fluid flow region. In this case, blood and dialysis fluid may be desirably configured to flow in the opposite directions to each other. The blood purifying filter 10 according to an embodiment of the present invention is not limited to the structure show in the drawing, and may be modified into other forms, including but not limited to a hemodialyzer, an adsorption filter column, or a hemodiafilter.

Figure 4:
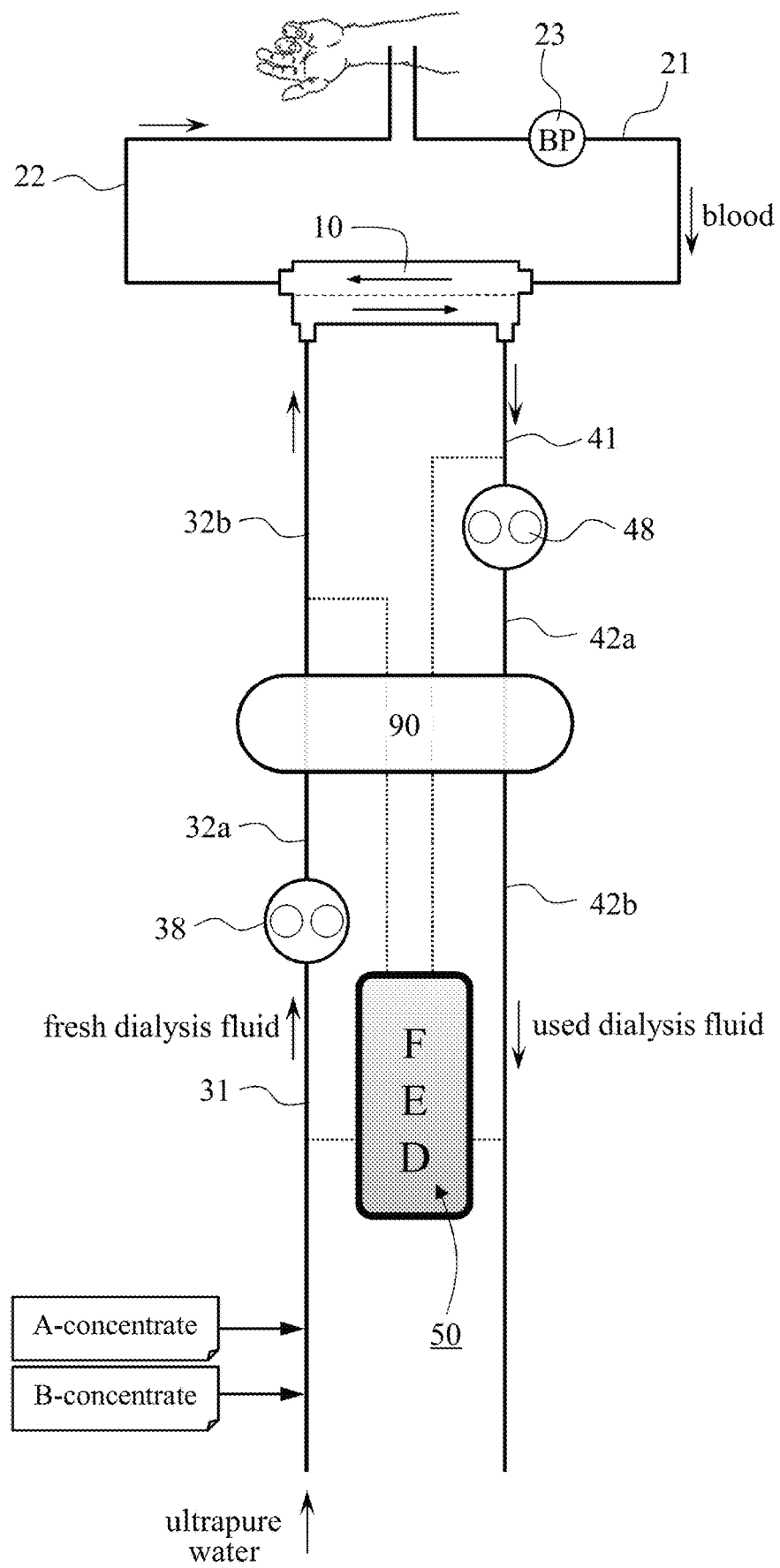
FIG. 4 is a view illustrating a blood purifying apparatus having a fluid pumping device named a filtration enhancing device (FED) according to an embodiment of the present invention.
Figure 5:
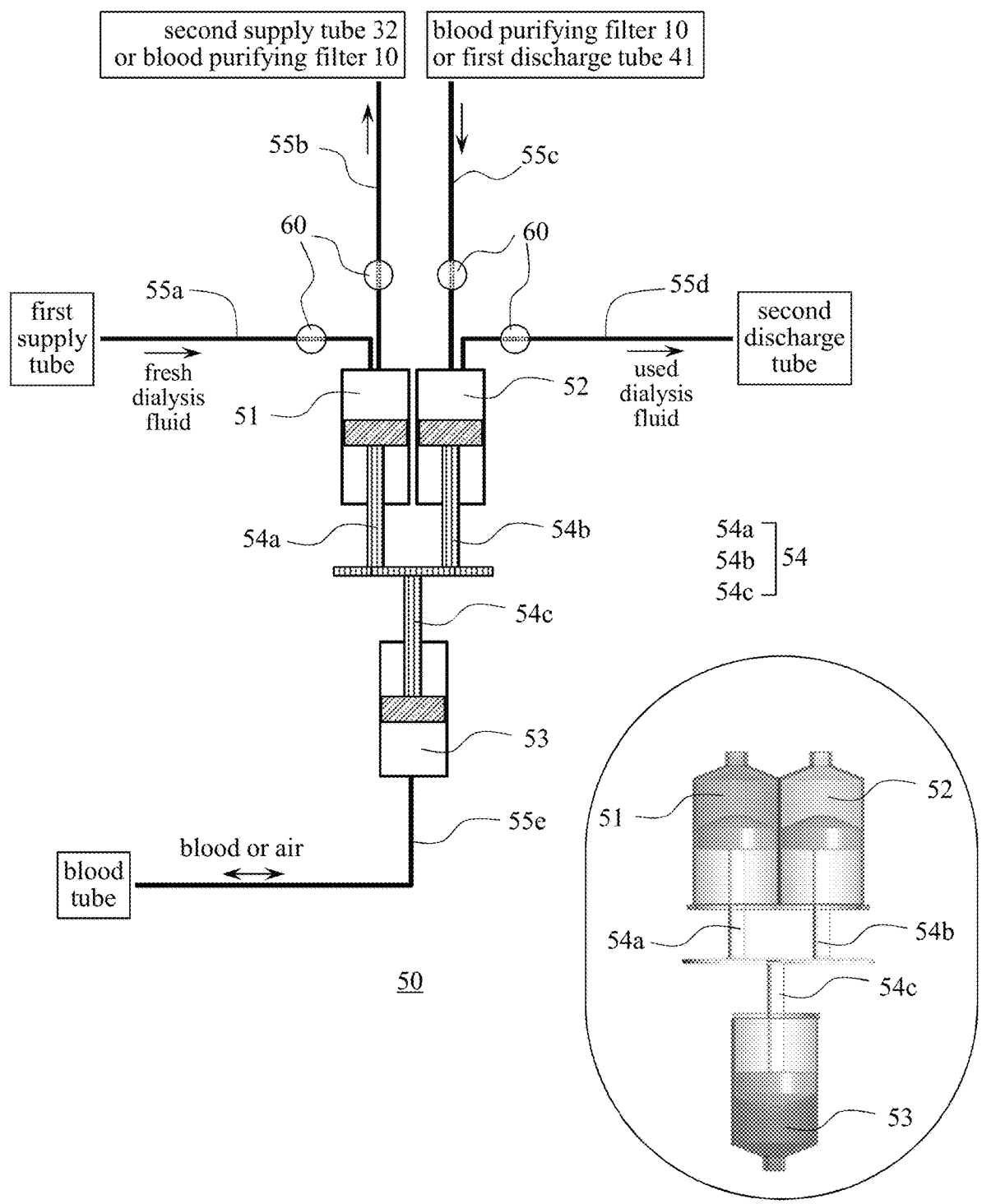
FIG. 5 is a view illustrating a fluid pumping device according to an embodiment of the present invention.

In addition, the blood purifying apparatus 1 according to an embodiment of the present invention may be additionally provided with a fluid pumping device 50. FIG. 4 is a view illustrating a blood purifying apparatus having a dialysis fluid pumping device 50. FIG. 5 illustrate a structure of the fluid pumping device 50 according to an embodiment of the present invention. The fluid pumping device 50 is capable of enhancing the total volume of filtration during the blood purification treatment, and thus it may be named a filtration enhancing device (FED).

As shown in FIG. 5, the fluid pumping device 50 may include a plurality of fluid chamber each having an internal space, such as a first chamber 51, a second chamber 52, and a third chamber 53. The fluid pumping device 50 may also include a chamber pressurizing member 54 which compresses or expands the internal spaces of the chambers 51 to 53 so as to allow a fluid to flow through the chambers. Here, the fluid pumping device 50 may be provided with separate chamber pressurizing members for each of the chambers 51 to 53, such as a first chamber pressurizing member 54a for compressing or expanding the first chamber 51, a second chamber pressurizing member 54b for compressing or expanding the second chamber 52, and a third chamber pressurizing member 54c for compressing or expanding the third chamber 53. However, the chamber pressurizing member 54 may compress or expand the internal spaces of the chambers 51 to 53 at the same time (such as compressing a portion of the chambers while expanding the other portion of the chambers), operating using a single chamber pressurizing member driver (not shown).

As shown in FIG. 5, the chambers 51, 52, and 53 having a cylindrical shape and a piston-shaped chamber pressurizing member 54 disposed inside the chambers are provided. However, the chambers and the chamber pressurizing member are not limited to the structures shown in the drawing. For example, the chambers may have a form of a fluid sac having an internal space to accommodate or discharge a fluid, and in this case, the chamber pressurizing member may have a structure to expand or pressurize the sacs.

The chamber pressurizing member driver (now shown) allows the chamber pressurizing member 54 to reciprocate along a straight line to compress or expand the internal spaces of the chambers 51 to 53. As aforementioned, since the chamber pressurizing member 54 compresses or expands the chamber 51 to 53 simultaneously, a single chamber pressurizing member driver may be used to drive the chamber pressurizing member 54.

As shown in FIG. 5, the first chamber 51 may be connected to the first supply tube 31 and the second supply tube 32. Specifically, the first chamber 51 may be connected to the first supply tube 31 and the downstream second supply tube 32b when the balancing chamber 90 is provided. In addition, since the downstream second supply tube 32b is connected to the blood purifying filter 10 (such as, to the dialysis fluid inlet 15), the first chamber 51 may be connected to the first supply tube 31 and the blood purifying filter 10 (such as, to the dialysis fluid inlet 15).

In a similar manner, the second chamber 52 may be connected to the first discharge tube 41 and the second discharge tube 42. Specifically, the second chamber 52 may be connected to the first discharge tube 41 and the downstream second discharge tube 42b when the balancing chamber 90 is provided. In addition, since the first discharge tube 41 is connected to the blood purifying filter 10 (such as, to the dialysis fluid outlet 16), the second chamber 52 may be connected to the blood purifying filter 10 (such as, to the dialysis fluid outlet 16) and the downstream second discharge tube 42b.

Figure 6:
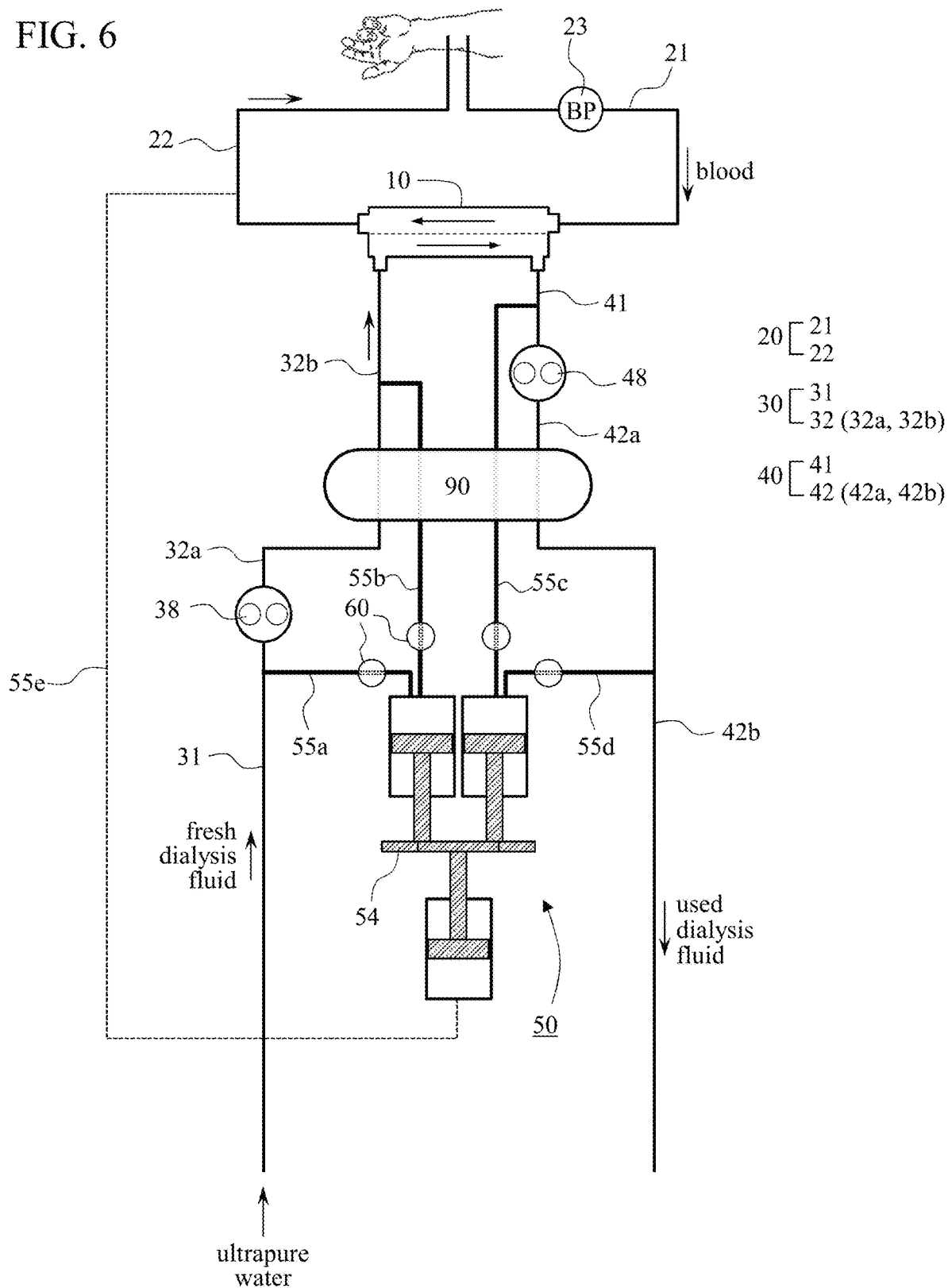
FIG. 6 is a view illustrating a blood purifying apparatus which is combined with a dialysis fluid pumping device according to an embodiment of the present invention.

In addition, as shown in FIG. 5 and FIG. 6, a first chamber tube 55a and a second chamber tube 55b may be provided for the connection between the first chamber 51 and the dialysis fluid supply tube 30. In addition, third chamber tube 55c and a fourth chamber tube 55d may be provided for the connection between the second chamber 52 and the dialysis fluid discharge tube 40. The first chamber 51 may be connected to the first supply tube 31 through the first chamber tube 55a where a fluid is supplied to the first chamber 51 and to the downstream second supply tube 32b through the second chamber tube 55b where a fluid is discharged from the first chamber 51. Likewise, the second chamber 52 may be connected to the first discharge tube 41 through the third chamber tube 55c where a fluid is supplied to the second chamber 52 and to the downstream second discharge tube 42b through the fourth chamber tube 55d where a fluid is discharged from the second chamber 52.

The third chamber 53 may be connected with the fifth chamber tube 55e through with a fluid is supplied to or discharged from the third chamber 53. Specifically, the third chamber 53 may be connected to the second blood tube 22 through the fifth chamber tube 55e. Also, the third chamber 53 may be connected to the first blood tube 21, or both of the first blood tube 21 and the second blood tube 22.

Fresh dialysis fluid flows through the first supply tube 31, the upstream second supply tube 32a, the downstream second supply tube 32b, the first chamber tube 55a, and the second chamber tube 55b. Used dialysis fluid flows through the first discharge tube 41, the upstream second discharge tube 42a, the downstream second discharge tube 42b, the third chamber tube 55c, and the fourth chamber tube 55d.

The fluid pumping device 50 may further include a flow controller 60 which regulates flow passages through the first chamber tube 55a, the second chamber tube 55b, the third chamber tube 55c, and the fourth chamber tube 55d. The flow controller 60 controls the inflow and outflow through the first chamber 51 and the second chamber 52.

Here, the chambers 51 to 53 may have substantially the same stroke volume. The stroke volume of the chamber can be defined as a volume that is expanded or compressed by the chamber pressurizing member 54 when the chamber pressurizing member 54 moves upward or downward in the drawings. Since the chamber pressurizing member 54 moves upward or downward in a predetermined length, in order for the chambers 51 to 53 to have the same expansion and compression stroke volume, the chambers 51 to 53 may have internal diameters that are substantially same as each other, when the chambers have a cylindrical shape.

However, the stroke volumes of the chambers 51 to 53 are not limited thereto. In an embodiment, while the first chamber 51 and the second chamber 52 have the same internal diameter, the third chamber 53 may have an internal diameter that is different from that of the first chamber 51 and the second chamber 52. Thus, the expansion and compression stroke volume of the third chamber 53 may be smaller or larger than the stroke volume of the first chamber 51 and the second chamber 52. For instance, while the first chamber 51 and the second chamber 52 may have the same stroke volume as each other, the third chamber 53 may have a stroke volume which is approximately a half of the stroke volume of the first chamber 51 or the second chamber 52. Also, in an extension, the first chamber 51 and the second chamber 52 may have a different stroke volume from each other.

According to an embodiment of the present invention, due to the operation of the chamber pressurizing member 54, the first chamber 51 and the second chamber 52 may be compressed at the same time, and in this case, the third chamber 53 may be expanded. Or, due to the operation of the chamber pressurizing member 54, the first chamber 51 and the second chamber 52 may be expanded while the third chamber 53 is compressed. However, the chambers operation is not limited to what is described. For instances, all of the chambers may be compressed and expanded at the same time. The chamber pressurizing member driver includes various structures that can compress or expand the chambers by pushing or pulling the chamber pressurizing member 54.

Figure 7:
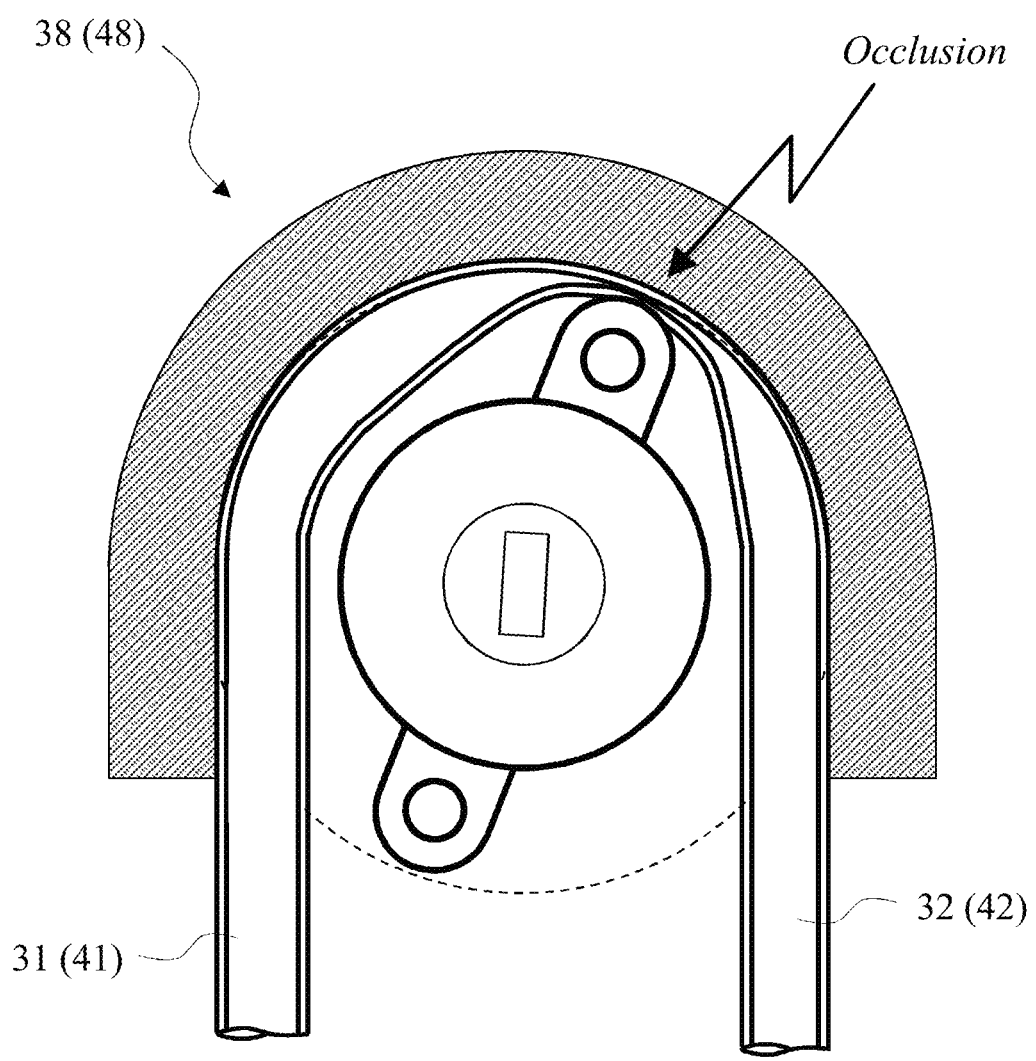
FIG. 7 is a view illustrating an exemplary dialysis fluid pump according to an embodiment of the present invention.

FIG. 7 is a view illustrating the exemplary dialysis fluid pumps 38 and 48 according to an embodiment of the present invention. A roller pump or a peristaltic pump is illustrated in FIG. 7. However, the dialysis fluid pumps 38 and 48 may be modified into other pumps, including a gear pump, a diaphragm pump, a piston pump, a rotary piston pump, and the like. Any pumping method which can transfer fluid through the dialysis fluid supply tube 30 and the dialysis fluid discharge tube 40 may be used for the dialysis fluid pumps 38 and 48. In addition, when a roller pump or a peristaltic pump is used for the dialysis fluid pumps 38 and 48, the roller may be able to block the flow passage through a portion of the dialysis fluid tubes, as shown in FIG. 7.

Figure 10:
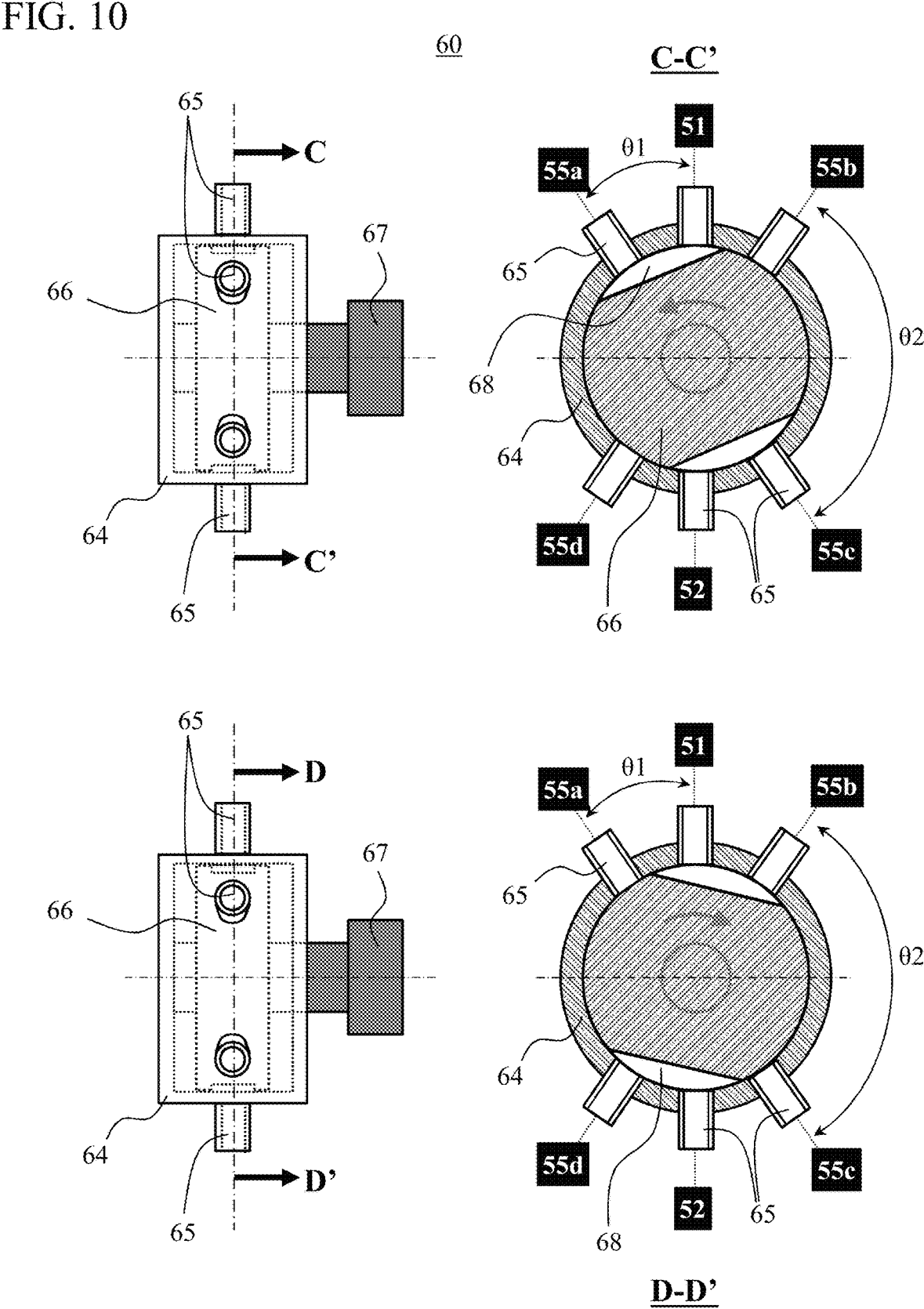

The flow controller 60 controls a flow passage through the tubes 55a, 55b, 55c, and 55d. Specifically, the flow controller 60 may block a flow passages through the tubes 55a and 55c and the tubes 55b and 55d in an alternate manner. For example, due to the operation of the flow controller 60, while the first chamber tube 55a and the third chamber tube 55c are blocked, the second chamber tube 55b and the fourth chamber tube 55d may be opened. On the other hand, when the first chamber tube 55a and the third chamber tube 55c are opened, the second chamber tube 55b and the fourth chamber tube 55d may be blocked. FIGS. 8 to 10 are views illustrating exemplary flow controllers 60 according to an embodiment of the present invention. The flow controller 60 may block the flow passage at least two of the tubes 55a, 55b, 55c, and 55d all the time.

As shown in FIG. 8, the flow controller 60 may have a structure in which a flow blocking member 61 reciprocates in a straight line to compress the tubes 55a and 55c or the tubes 55b and 55d while a flow-blocking wall 62 supports the tubes 55a, 55b, 55c and 55d which are compressed by the flow-blocking member 61. Here, a flow-blocking member driver (not shown) provides a straight force to the flow-blocking member 61. When the flow-blocking member 61 moves to the tube 55a and 55c, one end of the flow-blocking member 61 compresses the tubes supported by the flow-blocking wall 62 and blocks the flow passage therethrough. At this time, flow passages through the tube 55b and 55d are opened. Similarly, the flow-blocking member moves to the tubes 55b and 55d, and the other end of the flow-blocking member 61 compresses the tubes supported by the flow-blocking wall 62 and blocks the flow passage therethrough.

The flow-blocking member driver may include various structures that can apply a reciprocating movement force to the flow-blocking member 61. An exemplary flow-blocking member driver may include a cam for pushing the flow-blocking member 61 toward the flow-blocking wall 62 supporting the dialysis fluid tubes and a motor for rotating the cam. When the flow-blocking member 61 compresses the dialysis fluid tube due to the rotation of the cam, the flow passage therethrough may be blocked.

FIGS. 9 and 10 are views illustrating another example of the flow controller 60. The flow controller 60 may be configured to include a flow control housing 64 having an internal space, a plurality of flow control ports 65 disposed on the flow control housing 64, a flow control rotor 66 which is disposed inside the flow control housing 64 and tightly attached to an inner surface of the flow control housing 64, and a rotor driver 67 rotating the flow control rotor 66. In order for the flow control rotor 66 to rotate inside the flow control housing 64, the flow control rotor 66 and the internal space of the flow control housing 64 may have a cylindrical shape. Due to the rotation of the flow control rotor 66, a flow passage may be connected between two or more of the flow control ports 65.

The flow control rotor 66 may be configured to be tightly attached to the inner surface of the flow control housing 64 to thereby prevent a leakage of fluid through a contact surface of the flow control rotor 66 and the flow control housing 64. The flow control rotor 66 and the flow control housing 64 may be made of materials that can prevent a fluid from passing through the contact surface such as polymer. In addition, in order to prevent a leakage of any fluid through the contact surface, the flow control rotor 66 may be provided with a groove for an o-ring or a gasket that may be made of flexible materials such as rubber or silicone. The o-ring or gasket may also be made of hard materials such as metal, aluminum, plastic, polymer, and the like. Alternatively, the groove for an o-ring or a gasket may be formed on the flow control housing 64. The flow controller 60 according to an embodiment of the present invention may have various structures to prevent a fluid leakage through the contact surface between the flow control rotor 66 and the flow control housing 64.

As shown in FIG. 10, the flow controller 60 may include six flow control ports 65, which are connected to the first chamber 51, the first chamber tube 55a, the second chamber tube 55b, the second chamber 52, and the third chamber tube 55c, and the fourth chamber tube 55d, respectively. When the flow control rotor 66 rotates in one direction such as counterclockwise, as shown in FIG. 10 at the top, the flow passage may be connected between two flow control ports 65 which are connected to the first chamber tube 55a and the first chamber 51. Thus, the flow passage is opened between the first chamber tube 55a and the first chamber 51. Also, the flow passage between two flow ports 65 connected to the third chamber tube 55c and the third chamber 53, respectively, may be connected, which allows the flow passage between the third chamber tube 55c and the third chamber 53 to be opened. However, a flow passage between two flow ports 65 connected to the first chamber 51 and the second chamber tube 55b, respectively, and a flow passages between two flow ports 65 connected to the second chamber 52 and the fourth chamber tube 55d, respectively, are both blocked.

As the flow control rotor 66 further rotates in the same direction such as counterclockwise or in an opposite direction such as clockwise, the opening and blocking of the flow passage through the flow control ports 65 may be changed. For example, as shown in FIG. 10 at the bottom, as the flow control rotor 66 rotates clockwise, the flow passage may be opened between the first chamber 51 and the second chamber tube 55b and between the second chamber 52 and the fourth chamber tube 55d. However, at the same time, the flow passage is blocked between the first chamber 51 and the first chamber tube 55a and between the second chamber 52 and the third chamber tube 55c.

In an embodiment, the flow control ports 65 are formed in the flow control housing 64 and spaced apart from each other along a circumferential direction of the internal space of the flow control housing 64 which has a cylindrical shape. In addition, the flow control ports 65 may be placed within substantially the same cross-sectional plane which is perpendicular to an axial direction of the internal space of the flow control housing 64. For example, the flow control ports 65 of FIG. 10 are formed within a cross-sectional plane of C-C' or D-D'. Here, one of ordinary skill in the art may be aware that the same plan means that the flow control ports 65 can be placed at the substantially similar elevation along an axial direction of the flow control rotor 66, not merely exactly the same plane. In addition, when the flow control rotor 66 is coupled to the flow control housing 64, the flow control ports 65 which are formed on the flow control housing 64 may be configured to face the flow control rotor 66 at a middle portion of the flow control rotor 66 along an axial direction of the flow control rotor 66.

When the flow control ports 65 are placed within the same plane, an angle between two adjacent flow control ports 65 with respect to the axial center of the flow control rotor 66 can be defined. The angles between two adjacent flow control ports 65 with respect to the axial center of the flow control rotor 66 may be constant or may not be constant having a value that is different from each other. For example, the angle between two flow control ports 65 connected to the first chamber 51 and the first chamber tube 55a, respectively, has a value of $\theta 1$, and the angle between two flow control ports 65 connected to the second chamber tube 55b and the third chamber tube 55c, respectively, may have a value of $\theta 2$ which is larger than θ1. Also, the angle between two flow control ports 65 connected to the first chamber 51 and the second chamber tube 55*b*, respectively, may have a value that is substantially same as θ1.

The flow control rotor 66 according to an embodiment of the present invention may be configured to rotate unidirectionally or bidirectionally. FIG. 10 illustrates the flow controller 60 in which the flow control rotor 66 rotates counterclockwise (above) and clockwise (below). The time for opening or blocking the flow passage can be controlled by regulating the rotation speed of the flow control rotor 66.

In addition, the flow control rotor 66 may be further formed with a recessed portion 68 to facilitate fluid to flow through two adjacent flow control ports 65 where the flow passage is opened. The recessed portion 68 has a cross-sectional shape of a crescent moon in FIG. 10, but the cross-sectional shape of the recessed portion 68 may be modified into other shapes such as rectangular, square, quadrilateral, or triangular shapes.

The flow controller 60 is not limited to the structures shown in FIGS. 8 and 10 and may be modified into other structures that can serves as a means of opening or closing the flow passage through the first chamber tube 55*a* and the second chamber tube 55*b*, the third chamber tube 55*c*, and the fourth chamber tube 55*d*. In addition, the flow controller 60 according to an embodiment of the present invention may have a form of a solenoid valve, a rotary valve, an on-off valve, a one-way check valve, and the like.

Figure 11:
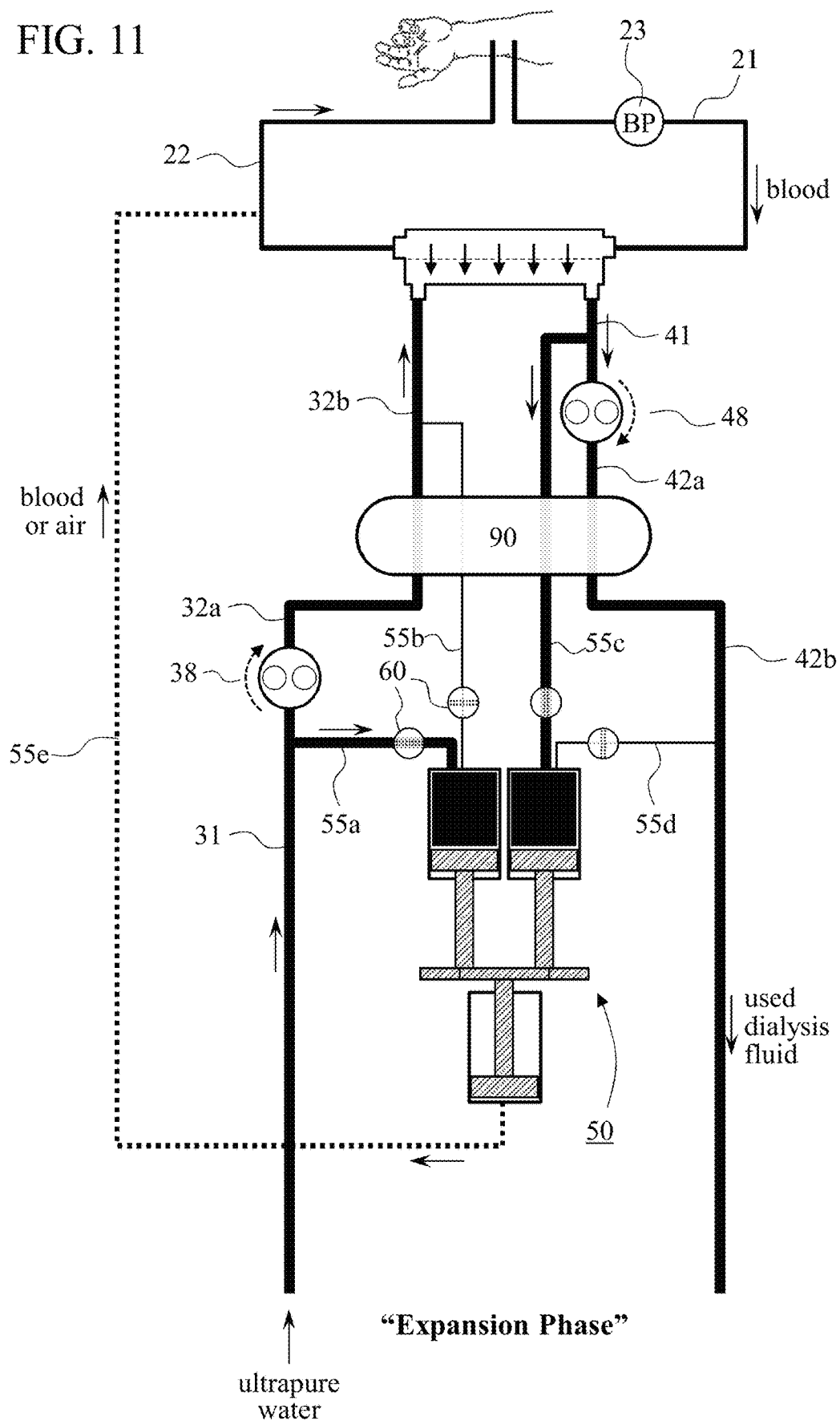
FIGS. 11 to 14 are views illustrating an operation of a fluid pumping device and a blood purifying apparatus according to an embodiment of the present invention.
Figure 14:
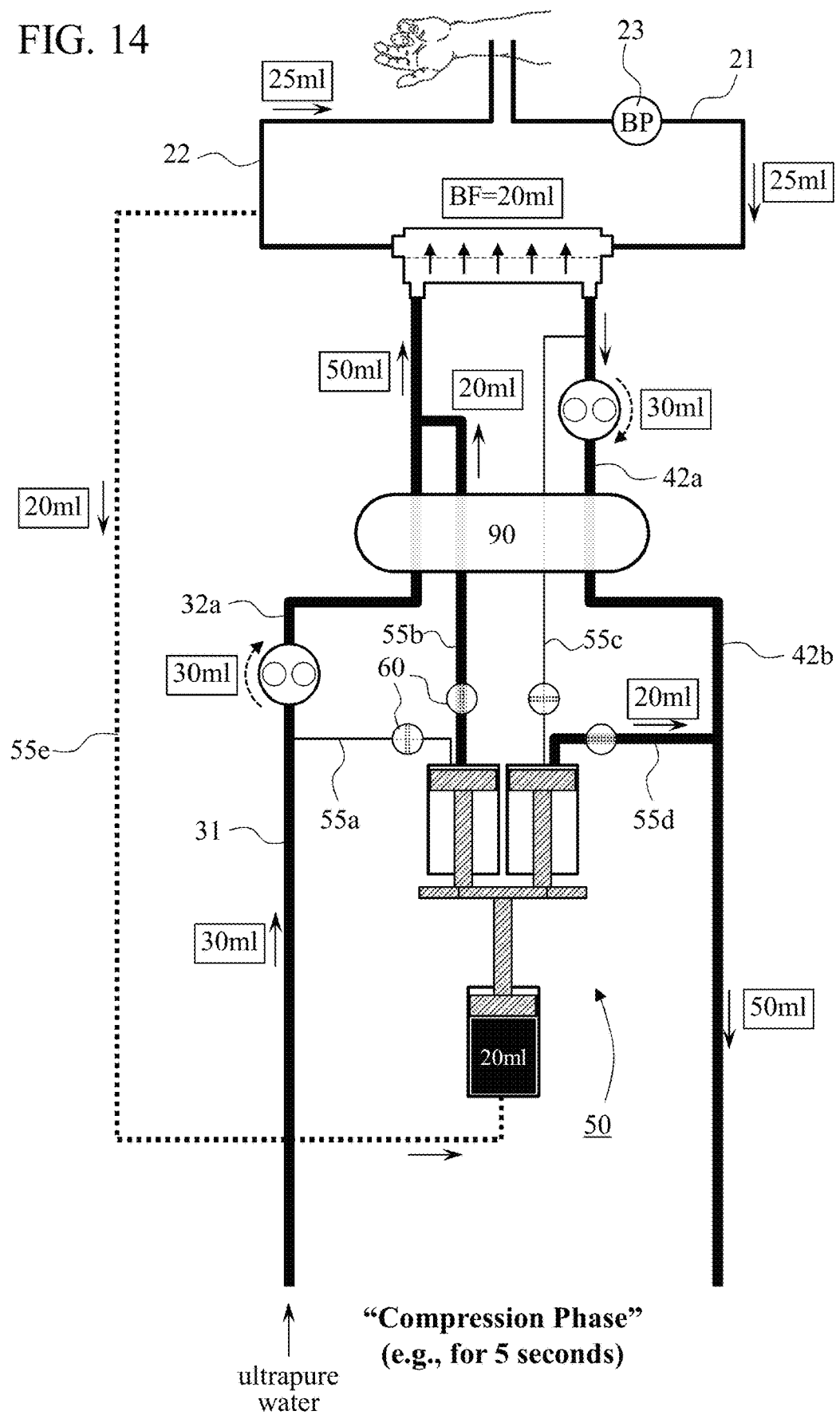

FIGS. 11 and 14 illustrate an operation of the blood purifying apparatus 1 having the fluid pumping device 50 according to an embodiment of the present invention.

As shown in FIG. 11, the blood pump 23 transfers blood at a predetermined rate, and the dialysis fluid pumps 38 and 48 each transfer a predetermined amount of dialysis fluid through the blood purifying filter 10. The first chamber 51 and the second chamber 52 of the fluid pumping device 50 are expanded and the third chamber 53 is compressed. In addition, the flow controller 60 blocks flow passages through the second chamber tube 55*b* and the fourth chamber tube 55*d*, and opens flow passages through the first chamber tube 55*a* and the third chamber tube 55*c*. Due to the expansion of the first chamber 51, fresh dialysis fluid flows into the first chamber 51. Due to the expansion of the second chamber 52, dialysis fluid of the blood purifying filter 10 flows into the second chamber 52. When the dialysis fluid of the blood purifying filter 10 flows into the second chamber 52, since the amount of the dialysis fluid supplied to the blood purifying filter 10 by the first dialysis fluid pump 38 is maintained at substantially the same rate as the amount of the dialysis fluid removed from the blood purifying filter 10 by the second dialysis fluid pump 48, the hydraulic pressure of dialysis fluid in the blood purifying filter 10 is lowered below the hydraulic pressure of blood, and filtration occurs. Water and waste products in blood move to the dialysis fluid flow region during the filtration. Here, since the third chamber 53 is compressed, air or blood stored in the third chamber 53 may be discharged to the second blood tube 22 so as to maintain the flow amount of blood returning back to a patient. This phase is named an "expansion phase."

Figure 12:
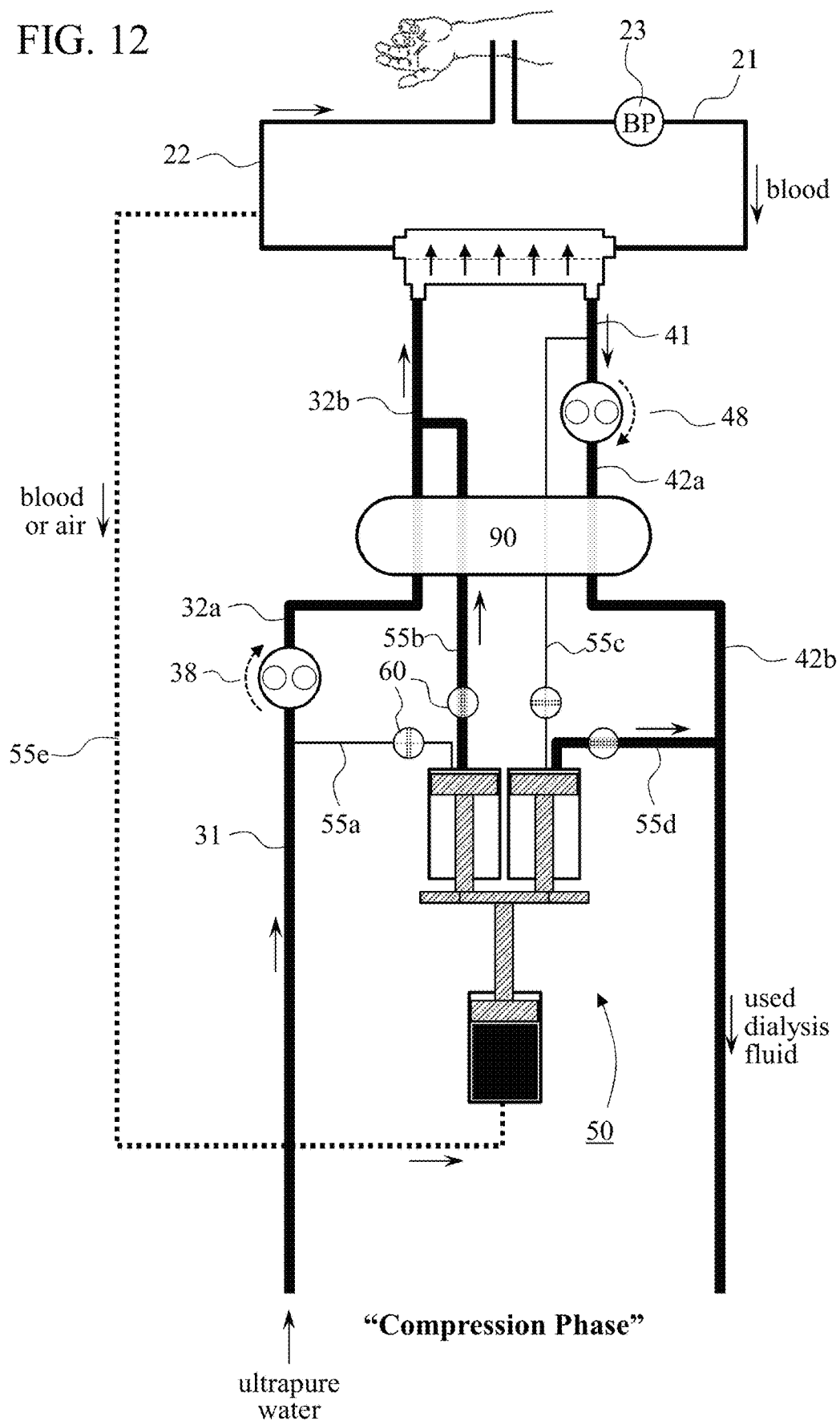

On the other hand, as shown in FIG. 12, while the blood pump 23 transfers blood at a predetermined rate and the dialysis fluid pumps 38 and 48 each transfer a predetermined amount of dialysis fluid through the blood purifying filter 10, the first chamber 51 and the second chamber 52 of the fluid pumping device 50 are compressed and the third chamber 53 is expanded. In addition, the flow controller 60 opens flow passages through the second chamber tube 55*b* and the fourth chamber tube 55*d*, and blocks flow passages through the first chamber tube 55*a* and the third chamber tube 55*c*. Due to the compression of the second chamber 52, dialysis fluid of the second chamber 52 is discarded therefrom. Due to the compression of the first chamber 51, dialysis fluid of the first chamber 51 is supplied to the blood purifying filter 10. When the dialysis fluid is supplied to the blood purifying filter 10, since the amount of the dialysis fluid removed from the blood purifying filter 10 by the second dialysis fluid pump 48 is maintained at substantially the same rate as the amount of the dialysis fluid supplied to the blood purifying filter 10 by the first dialysis fluid pump 38, the hydraulic pressure of dialysis fluid in the blood purifying filter 10 increases above hydraulic pressures of blood, and backfiltration occurs. Water in the dialysis fluid moves toward a blood flow region during the backfiltration. Here, since the third chamber 53 is expanded, a portion of blood or air may flow into the third chamber 53 so as to maintain the flow amount of blood returning back to a patient. This phase is named a "compression phase."

When the first chamber 51 and the second chamber 52 are compressed (that is, "compression phase"), a transmembrane pressure (TMP) of the blood purifying filter 10 has a negative (−) value and backfiltration occurs. On the other hand, the first chamber 51 and the second chamber 52 are expanded (that is, "expansion phase"), the TMP becomes a positive (+) value and filtration occurs. The TMP can be defined as a pressure difference between the blood pressures and dialysis fluid pressures passing through the blood purifying filter 10. Thus, a cycle of expansion and compression of the first chamber 51 and the second chamber 52 configures a cycle of filtration and backfiltration, and in the blood purification treatment using the blood purifying apparatus 1 according to an embodiment of the present invention, the cycle of filtration and backfiltration is repeated, removing water and waste products during filtration and supplementing lost water during backfiltration.

Figure 13:
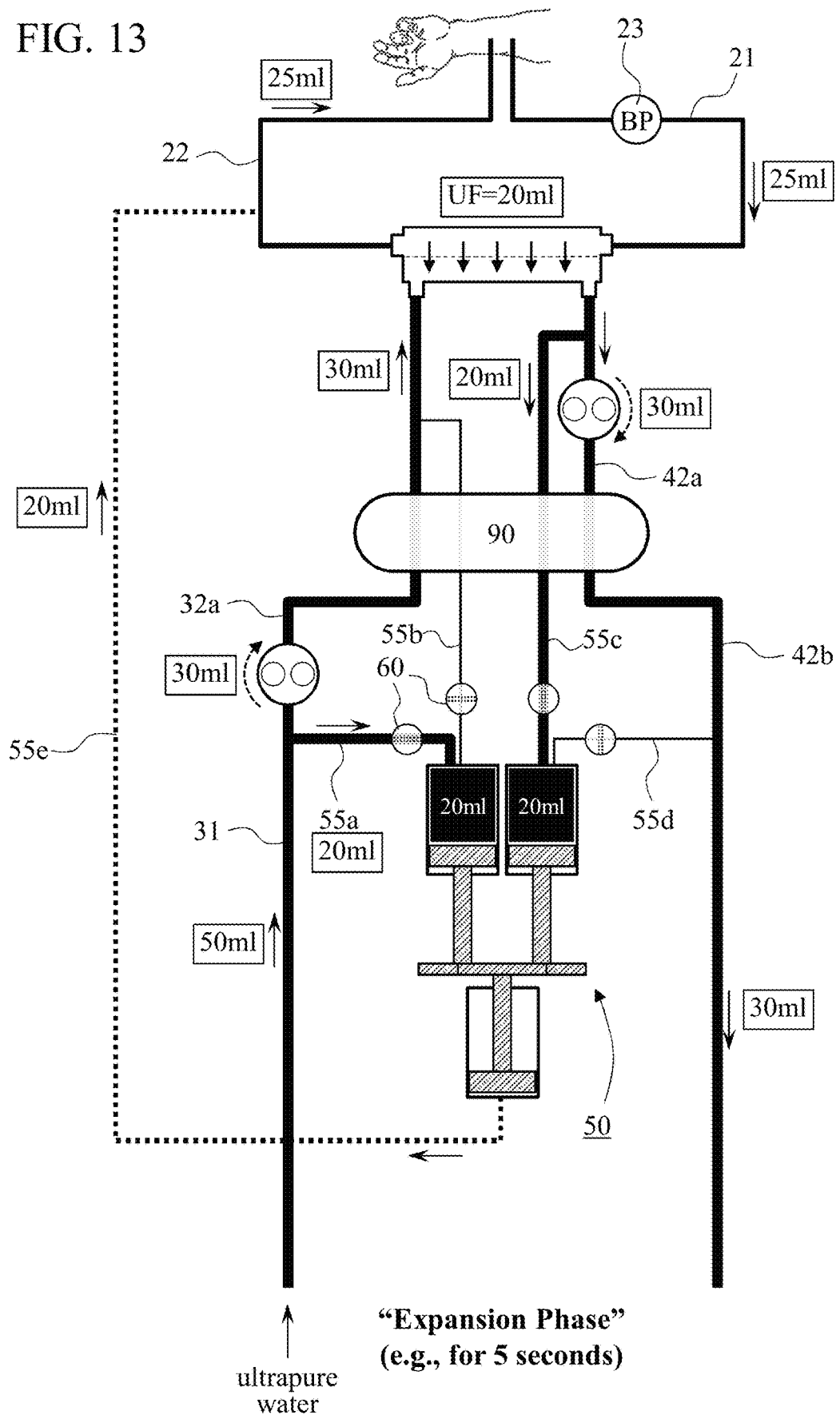

FIGS. 13 and 14 are views illustrating the operation of the fluid pumping device 50 and the blood purifying apparatus 1 according to an embodiment of the present invention, in which exemplary flow rates in the respective tubes are described. The stroke volume of the chambers is assumed 20 ml in this example. Blood flows at 300 ml/min by the blood pump 23. The first and second dialysis fluid pumps 38 and 48 each transfer 360 ml/min of dialysis fluid upstream and downstream of the blood purifying filter 10 and the balancing chamber 90 ensures the amount of the dialysis fluid supplied to and discharged from the blood purifying filter 10 to be maintained identically. It is assumed that one stroke of the expansion and compression phase takes 5 seconds (5 seconds/stroke), and thus, 12 strokes of the expansion and compression phases are repeated during a minute (12 strokes/min). As shown in FIGS. 13 and 14, the flow rate of blood returning to a patient through the second blood tube 22 is maintained at 25 ml for 5 seconds (i.e., 300 ml/min) regardless of the expansion or compression of the fluid pumping device 50. In addition, due to the operation of the blood pump 23, the flow rate of blood at the first blood tube 21 is also maintained uniformly—300 ml/min in this example. Despite pushing and pulling of dialysis fluid in the fluid pumping device 50, the flow rates of blood are maintained substantially uniformly upstream and downstream of the blood purifying filter 10.

During backfiltration (or the compression phase), a portion of blood or air flowing through the second blood tube 22 may be stored into the third chamber 53. During filtration (or the expansion phase), the blood or air stored in the third chamber 53 may be supplied to the second blood tube 22, thereby allowing the flow rate of blood returning to a patient to be substantially consistent. The third chamber 53 is illustrated as being connected to the second blood tube 22, but the third chamber 53 may be modified, for example, to be connected to the first blood tube 21, or both the first blood tube 21 and the second blood tube 22.

The fluid pumping device 50 according to an embodiment of the present invention is not limited to the structure shown in FIG. 5. The fluid pumping device 50 may have different structures to allow the hydraulic pressure of the dialysis fluid in the blood purifying filter 10 to quickly fluctuate above and below the pressure of blood. FIGS. 15 to 18 are views illustrating the blood purifying apparatus 1 and the fluid pumping device 50 according to another embodiment of the present invention.

Figure 15:
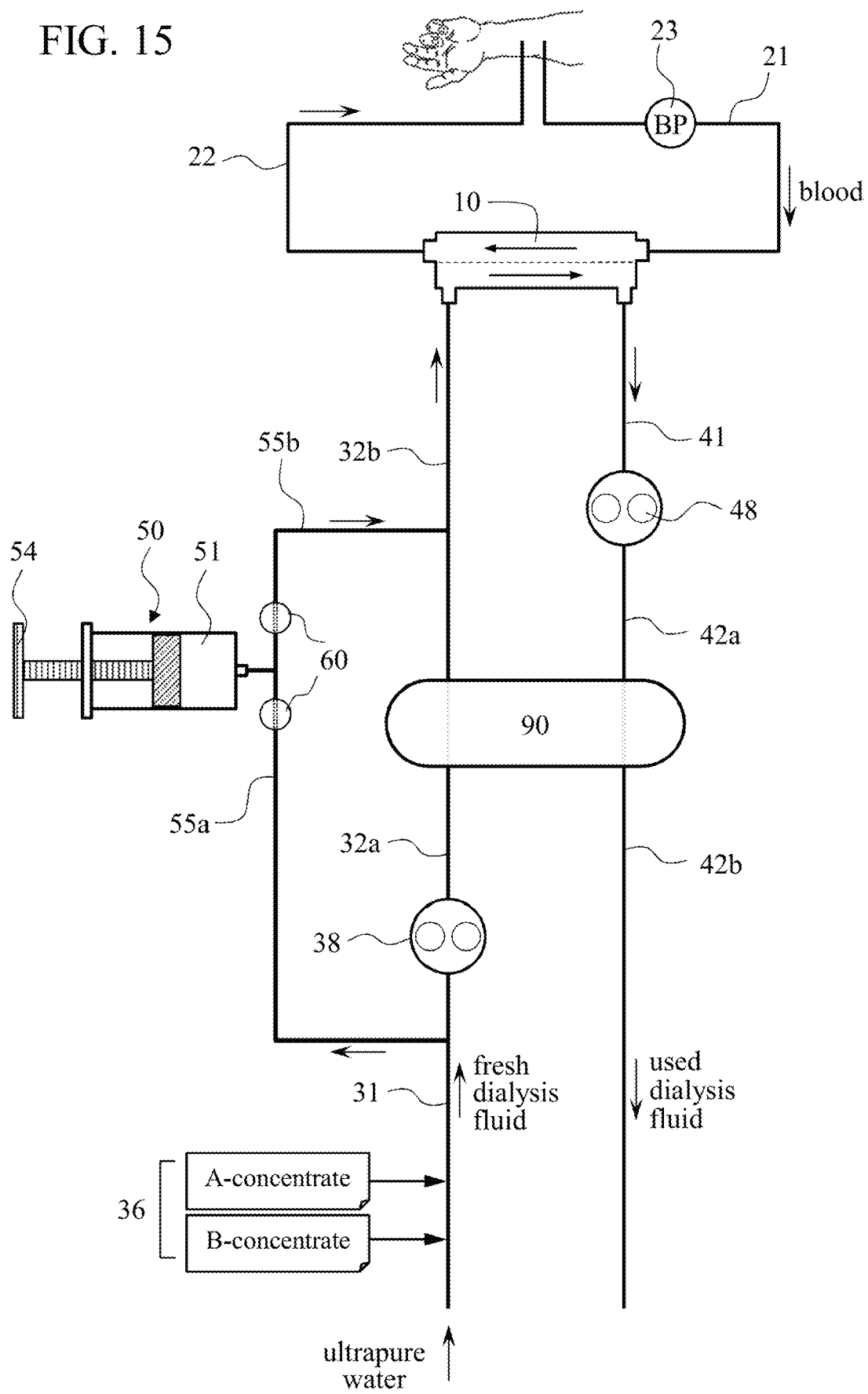
FIGS. 15 to 18 are views illustrating a blood purifying apparatus according to an embodiment of the present invention.
Figure 16:
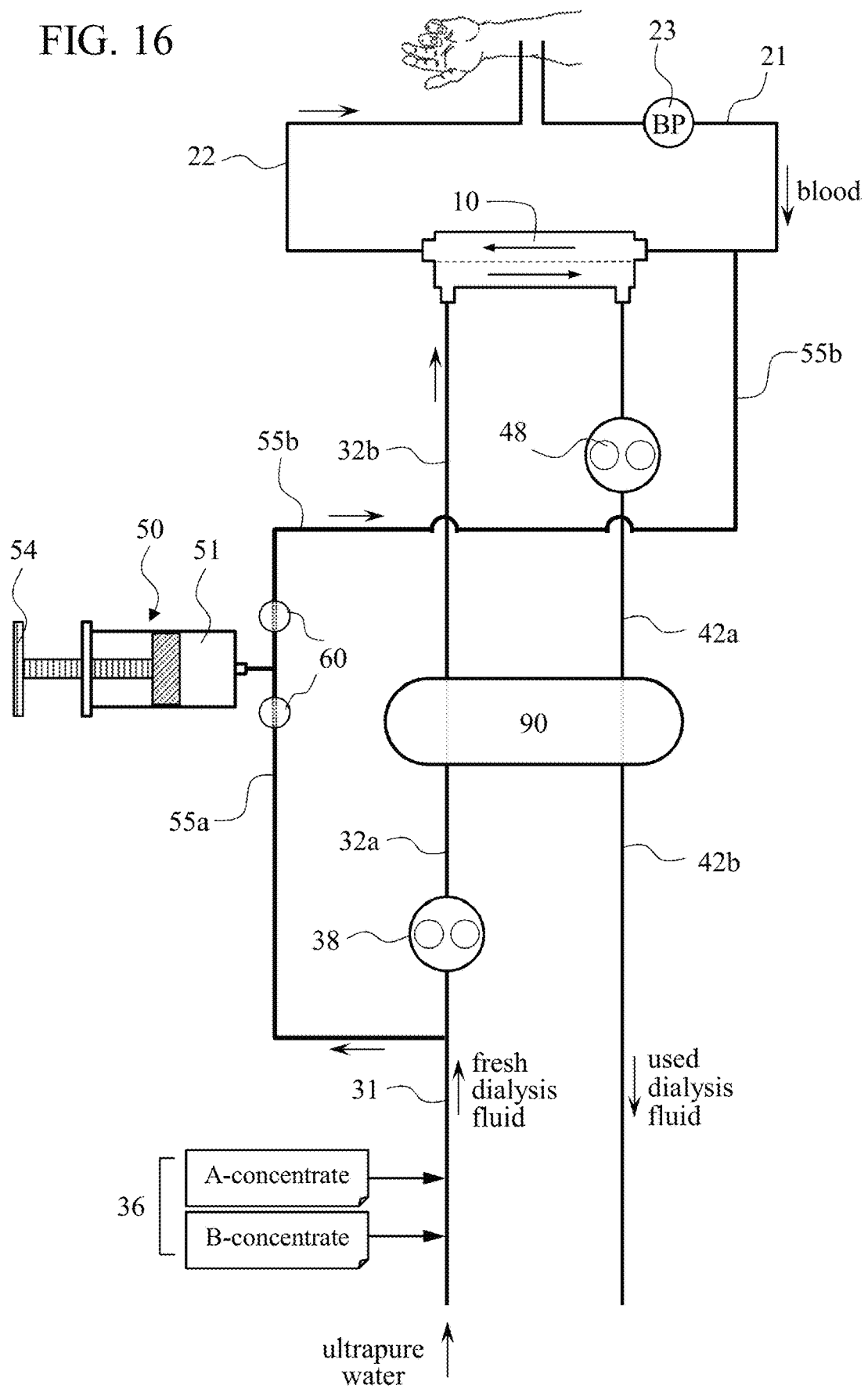

The fluid pumping device 50 according to an embodiment of the present invention may have a structure in which a single chamber 51 having an internal space and a single chamber pressurizing member 54 compressing or expanding the single chamber 51 are used. The chamber 51 may be connected to the first supply tube 31 through the first chamber tube 55a and the second supply tube 32 through the second chamber tube 55b. In particular, when the balancing chamber 90 is provided, the chamber 51 may be connected to the first supply tube 31 through the first chamber tube 55a and the downstream second supply tube 32b through the second chamber tube 55b, as depicted in FIG. 15. The flow controller 60 is provided to control the flow passage through the first chamber tube 55a and the second chamber tube 55b. The operation of the chamber 51, the chamber pressurizing member 54, and the flow controller 60 is described above.

Figure 17:
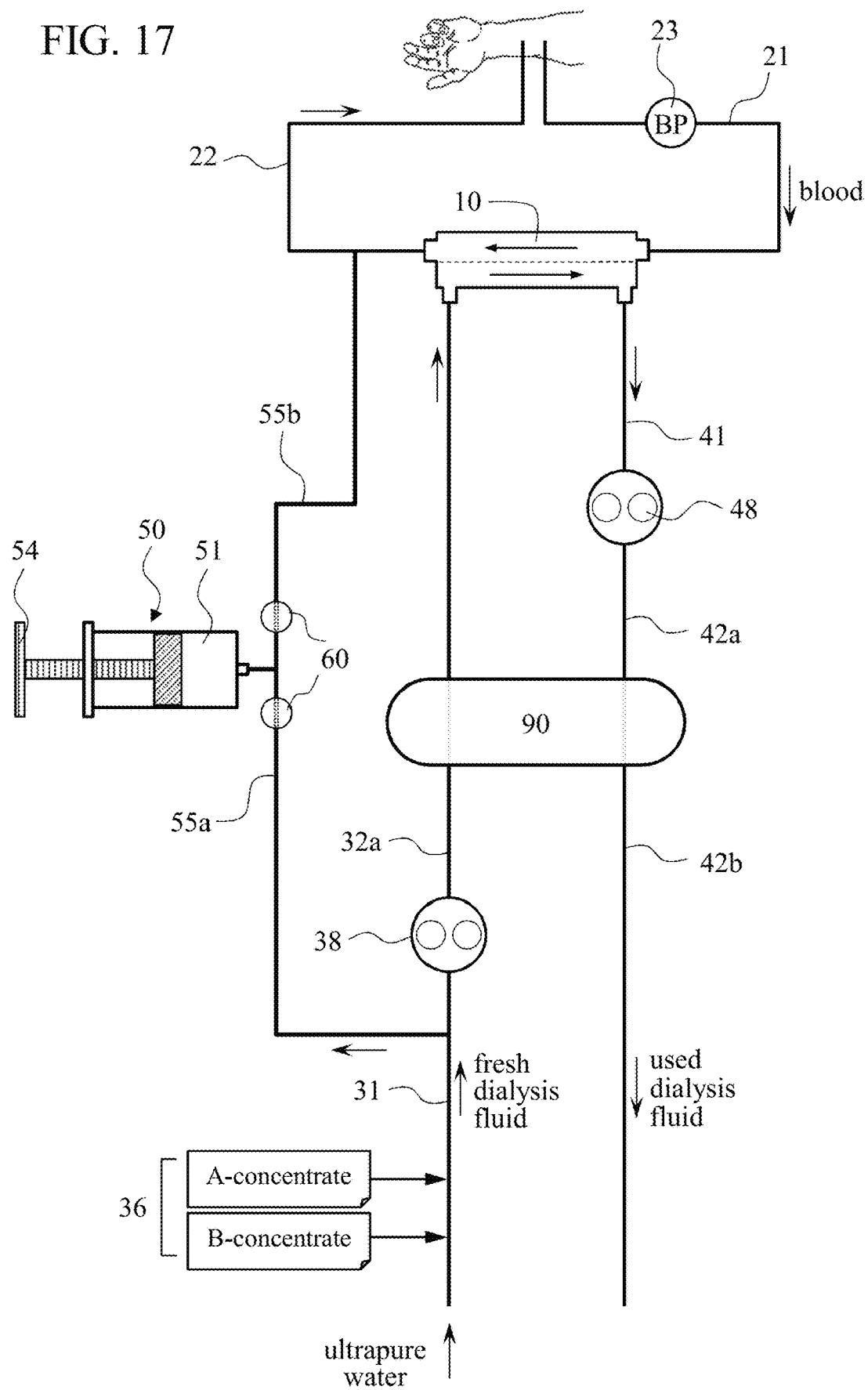
Figure 18:
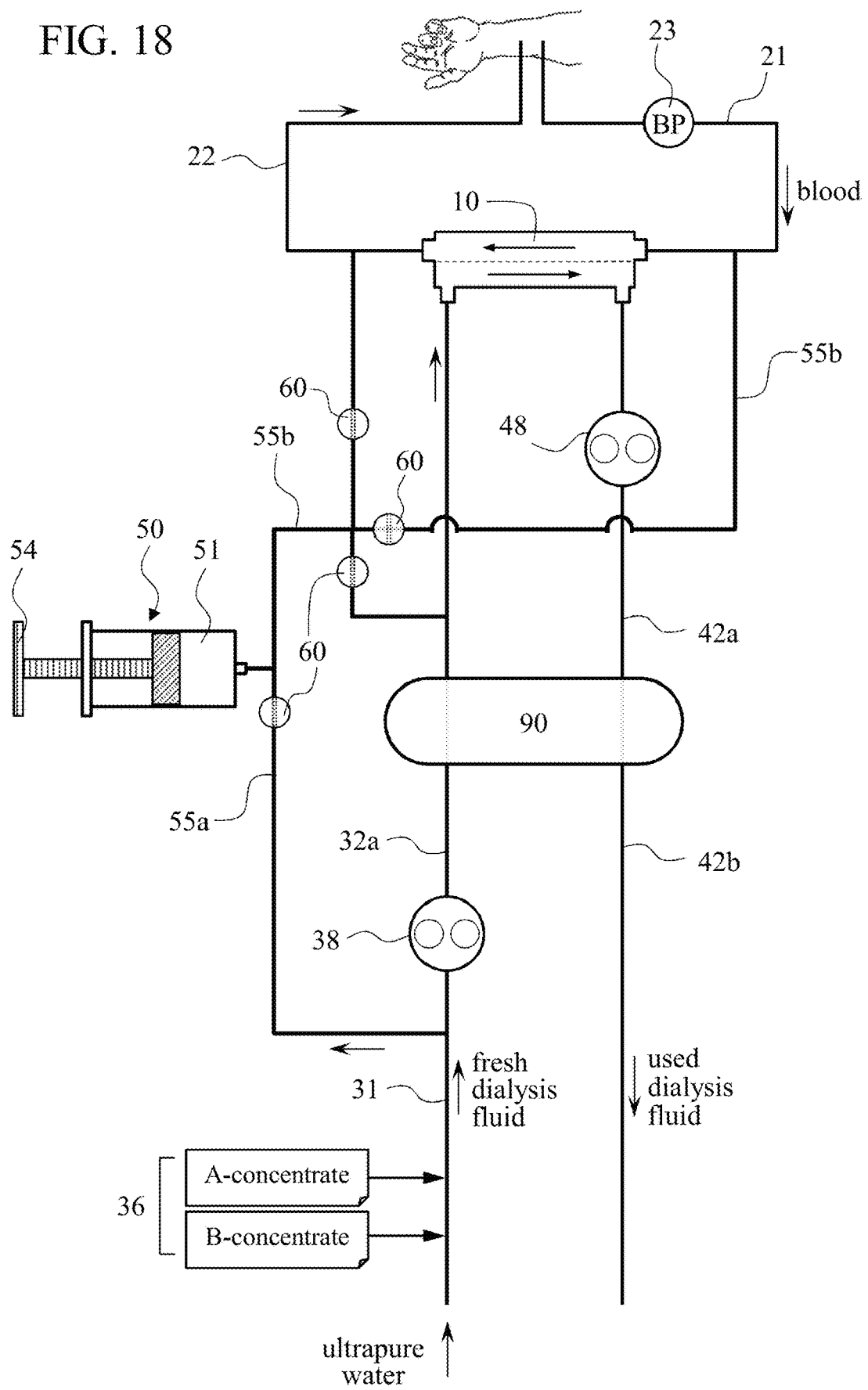

In addition, the fluid pumping device 50 may be modified such that the first chamber 51 may be connected to the first supply tube 31 and the first blood tube 21 (FIG. 16) or to the first supply tube 31 and the second blood tube 22 (FIG. 17). Alternatively, the first chamber 51 of the fluid pumping device 50 may be connected to the first supply tube 31, the second supply tube 32 (or the downstream second supply tube 32b), the first blood tube 21, and the second blood tube 22, as shown in FIG. 18. In this case, the flow controller 60 may be able to control the flow passages through the tubes connecting between the chamber 51 and the first supply tube 31, between the chamber 51 and the downstream second supply tube 32b, between the chamber 51 and the first blood tube 21, and/or between the chamber 51 and the second blood tube 22.

In addition, the blood purifying apparatus 1 may be further modified where the fluid pumping device 50 may be used as a principal means of transferring dialysis fluid, not merely as an auxiliary pumping device for the first or second dialysis fluid pump 38 or 48.

Figure 19:
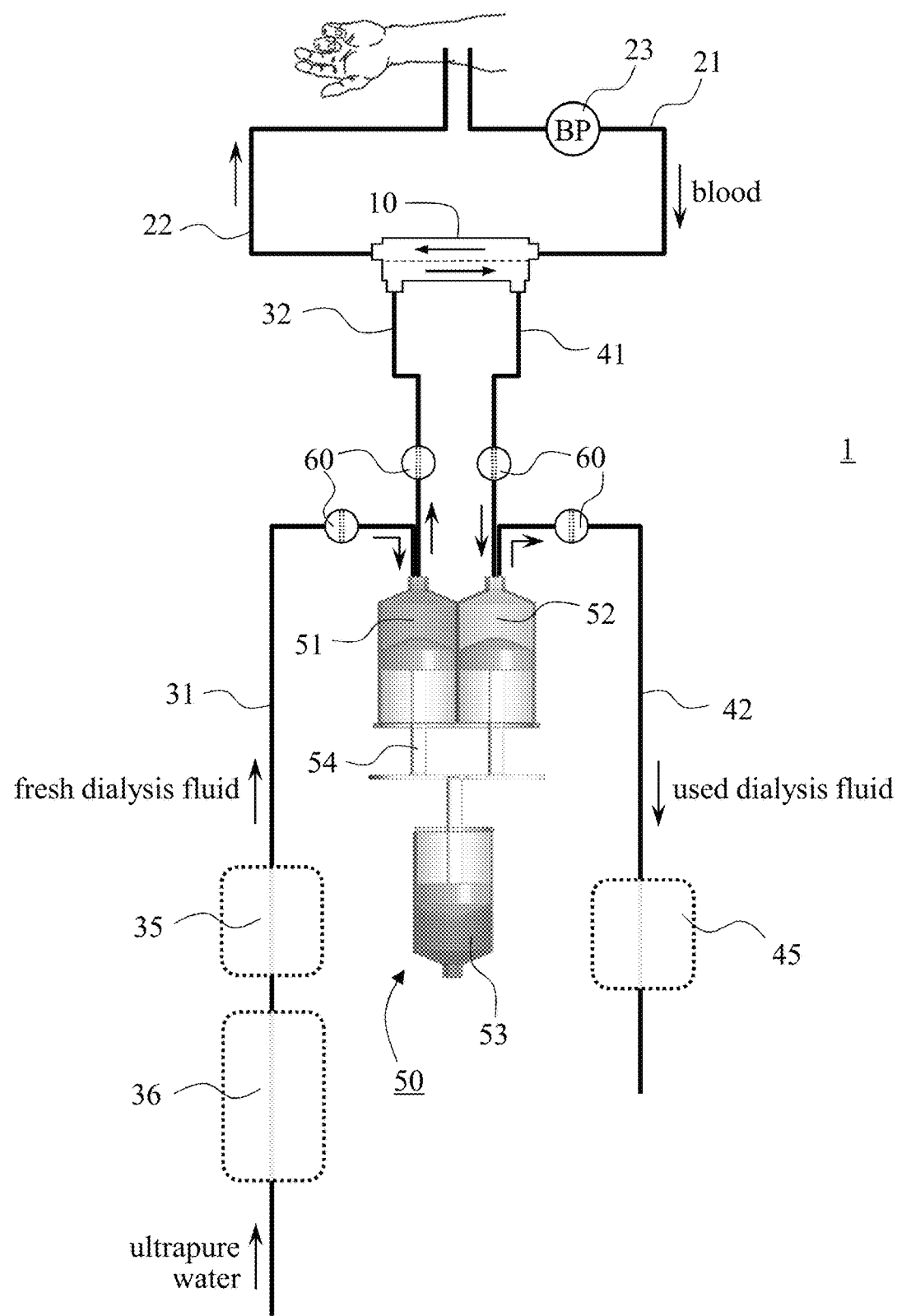
FIG. 19 is a view illustrating a blood purifying apparatus having a dialysis fluid pumping device as a means of transferring dialysis fluid according to an embodiment of the present invention.

FIG. 19 is a view illustrating the blood purifying apparatus 1 according to another embodiment of the present invention. As shown in FIG. 19, the first chamber 51 may be connected to the first supply tube 31 and the second supply tube 32, and the second chamber 52 may be connected to the first discharge tube 41 and the second discharge tube 42.

The flow controller 60 controls a flow passage through the tubes 31, 32, 41, and 42. Specifically, the flow controller 60 may block the flow passages through the tubes 31 and 41 and the tubes 32 and 42 in an alternate manner. For example, due to the operation of the flow controller 60, while the second supply tube 32 and the second discharge tube 42 are blocked, the first supply tube 31 and the second discharge tube 42 may be opened, or vice versa. FIGS. 8 to 10 are views illustrating the exemplary flow controller 60 according to an embodiment of the present invention.

Figure 20:
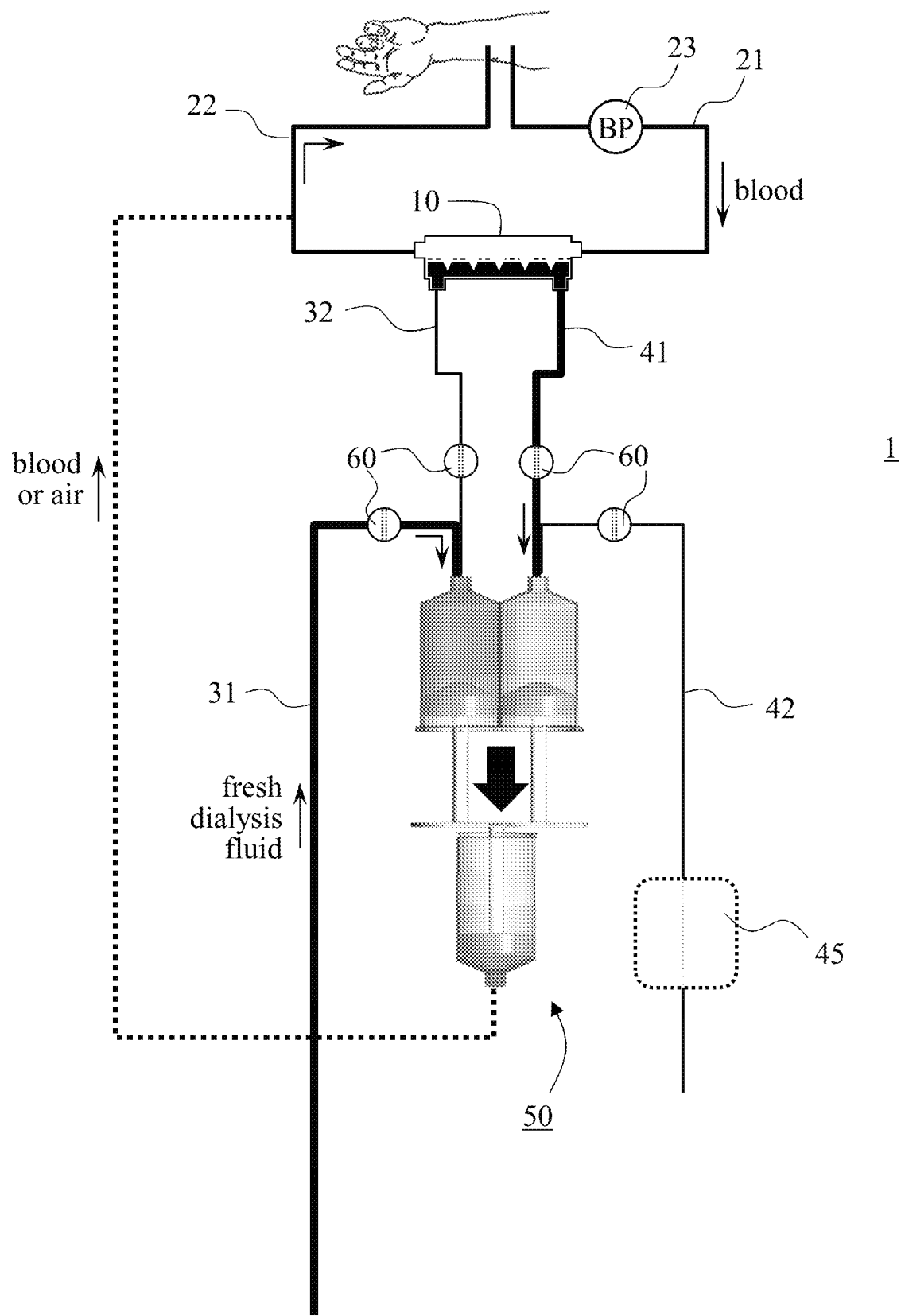
FIGS. 20 and 21 are views illustrating an operation of a fluid pumping device and a blood purifying apparatus according to another embodiment of the present invention.
Figure 21:
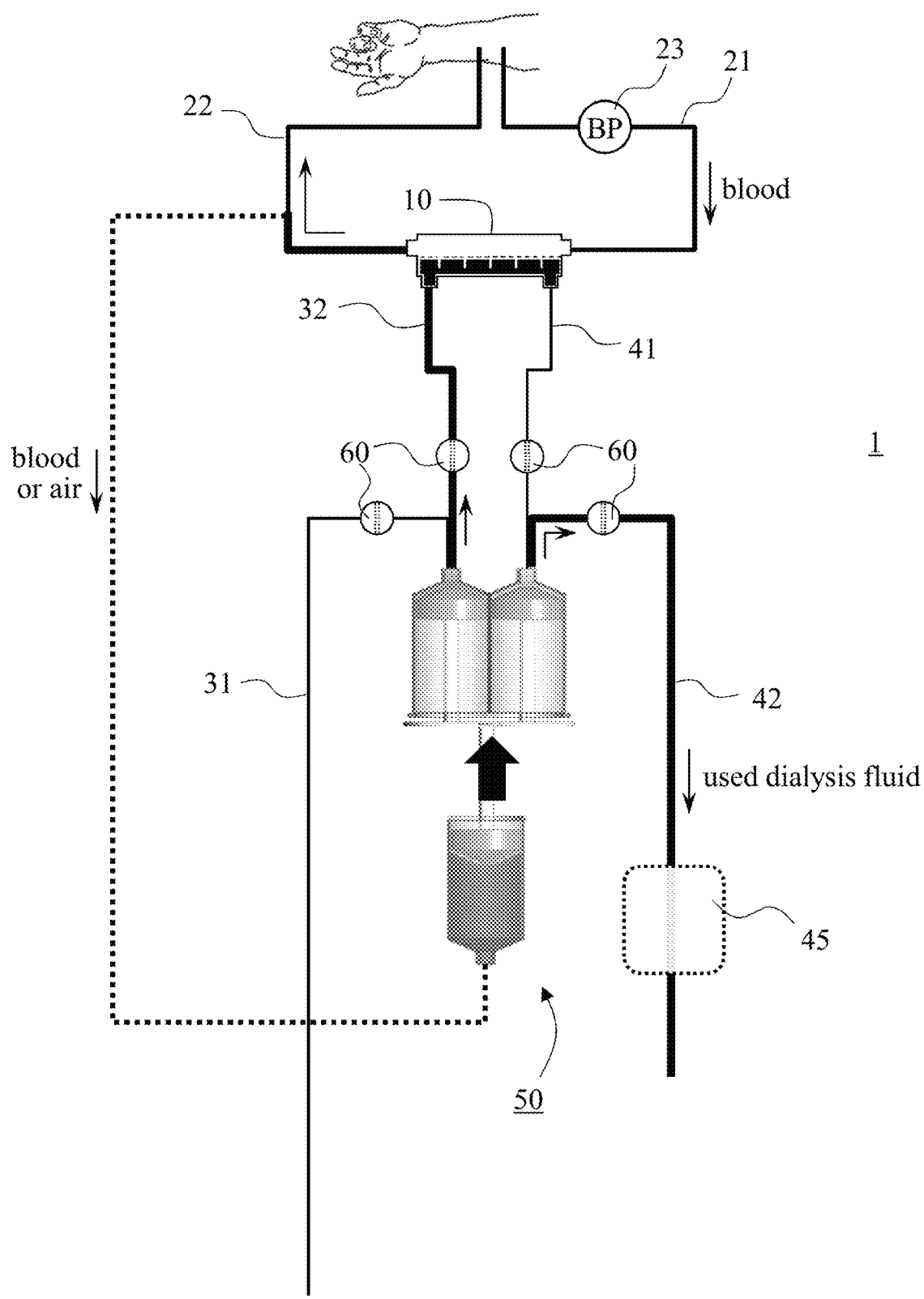

FIGS. 20 and 21 are views illustrating an operation of the blood purifying apparatus 1 according to an embodiment of the present invention.

As shown in FIG. 20, while the blood pump 23 transfers blood at a predetermined rate, the first chamber 51 and the second chamber 52 of the fluid pumping device 50 are expanded and the third chamber 53 thereof is compressed. In addition, the flow controller 60 blocks the second supply tube 32 and the second discharge tube 42, and opens the first supply tube 31 and the first discharge tube 41. Due to the expansion of the first chamber 51, dialysis fluid flows into the first chamber 51. Due to the expansion of the second chamber 52, dialysis fluid of the blood purifying filter 10 flows into the second chamber 52. When the dialysis fluid of the blood purifying filter 10 flows into the second chamber 52, since the second supply tube 32 is blocked, the hydraulic pressure of dialysis fluid in the blood purifying filter 10 is lowered below the hydraulic pressure of blood, and filtration in which water and waste products in blood move to the dialysis fluid flow region occurs. Here, since the third chamber 53 is compressed, blood or air stored in the third chamber 53 may be supplied to the second blood tube 22. This phase is named a "expansion phase."

On the other hand, as shown in FIG. 21, while the blood pump 23 transfers blood at a predetermined rate, the first chamber 51 and the second chamber 52 of the fluid pumping device 50 are compressed and the third chamber 53 thereof is expanded. In addition, the flow controller 60 opens the second supply tube 32 and the second discharge tube 42, and blocks the first supply tube 31 and the first discharge tube 41. Due to the compression of the second chamber 52, dialysis fluid of the second chamber 52 is discarded therefrom. Due to the compression of the first chamber 51, dialysis fluid of the first chamber 51 is supplied to the blood purifying filter 10. When the dialysis fluid is supplied to the blood purifying filter 10, since the first discharge tube 41 is blocked, the hydraulic pressure of dialysis fluid in the blood purifying filter 10 increases above the hydraulic pressure of blood, and backfiltration in which water in the dialysis fluid moves toward a blood flow region occurs. Here, since the third chamber 53 is expanded, a portion of blood or air flowing through the second blood tube 22 may flow into the third chamber 53. This phase is named an "compression phase."

When the first chamber 51 and the second chamber 52 are compressed, a TMP of the blood purifying filter 10 has a negative (−) value and backfiltration occurs. The first chamber 51 and the second chamber 52 are expanded, the TMP becomes a positive (+) value and filtration occurs. Thus, a cycle of expansion and compression of the first chamber 51 and the second chamber 52 configures a cycle of filtration and backfiltration, and in the blood purification treatment using the blood purifying apparatus 1 according to an embodiment of the present invention, the cycle of filtration and backfiltration is repeated, removing water and waste products during filtration and supplementing lost water during backfiltration.

During backfiltration (or the compression phase), a portion of blood or air flowing through the second blood tube 22 may be stored into the third chamber 53. During filtration (or the expansion phase), the blood or air stored in the third chamber 53 may be supplied to the second blood tube 22, thereby allowing the flow rate of blood returning to a patient to be consistent. The third chamber 53 is illustrated as being connected to the second blood tube 22, but the third chamber 53 may be modified, for example, to be connected to the first blood tube 21, or both the first blood tube 21 and the second blood tube 22.

Here, the first chamber 51 and the second chamber 52 may have substantially the same stroke volume while the third chamber 53 may have a stroke volume which is smaller than that of the first chamber 51 or the second chamber 52. Since the chamber pressurizing member 54 moves upward or downward in a predetermined length, each chamber's internal diameter may determine the stroke volume of the chamber when the chambers have a cylindrical shape. For example, in order for the third chamber 53 to have a stroke volume that is a half of the stroke volume of the first chamber 51 or the second chamber 52, it is desired that the cross-sectional area of the inner space of the third chamber 53 may be approximately a half of the cross-sectional area of the inner space of the first chamber 51 or the second chamber 52. Here, the cross-sectional area of the inner space may be an area of the surface dissected along a surface perpendicular to the axial direction of the cylindrical chamber.

Figure 22:
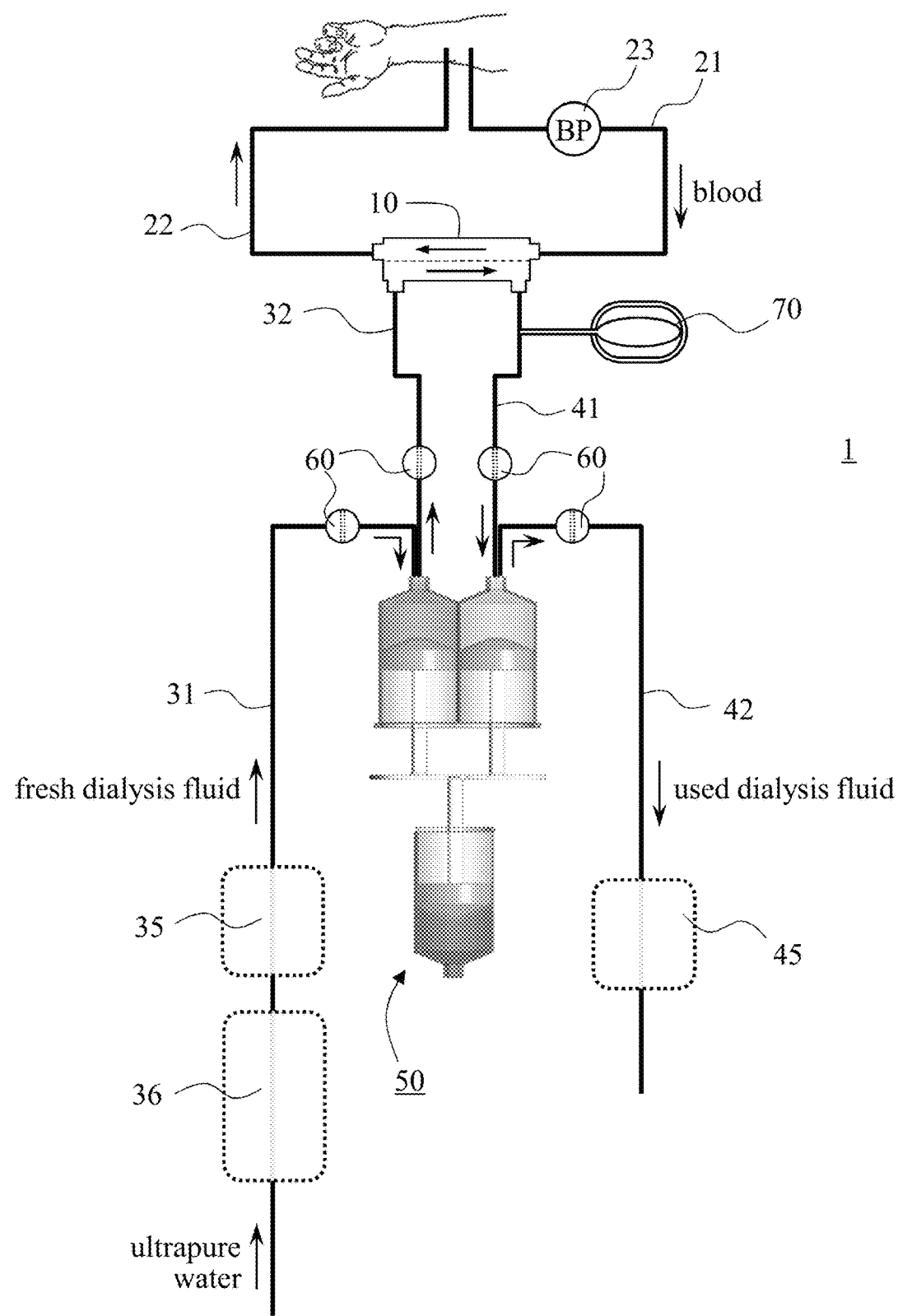
FIG. 22 is a view illustrating a blood purifying apparatus having a volume chamber according to an embodiment of the present invention.

The blood purifying apparatus 1 according to an embodiment of the present invention may further include a volume chamber 70 to store the dialysis fluid. As shown in FIG. 22, the volume chamber 70 may be connected to the first discharge tube 41. The internal space of the volume chamber 70 is expanded when dialysis fluid flows in, while it is contracted when dialysis fluid flows out. The volume chamber may be configured to include a container having a fixed space to accommodate dialysis fluid and a flexible bag placed inside the container. The volume chamber is not limited in the structures shown in the drawing and may be modified into other structures. The volume chamber 70 may be connected to the second supply tube 32 instead of the first discharge tube 41, or both the second supply tube 32 and the first discharge tube 41.

Figure 23:
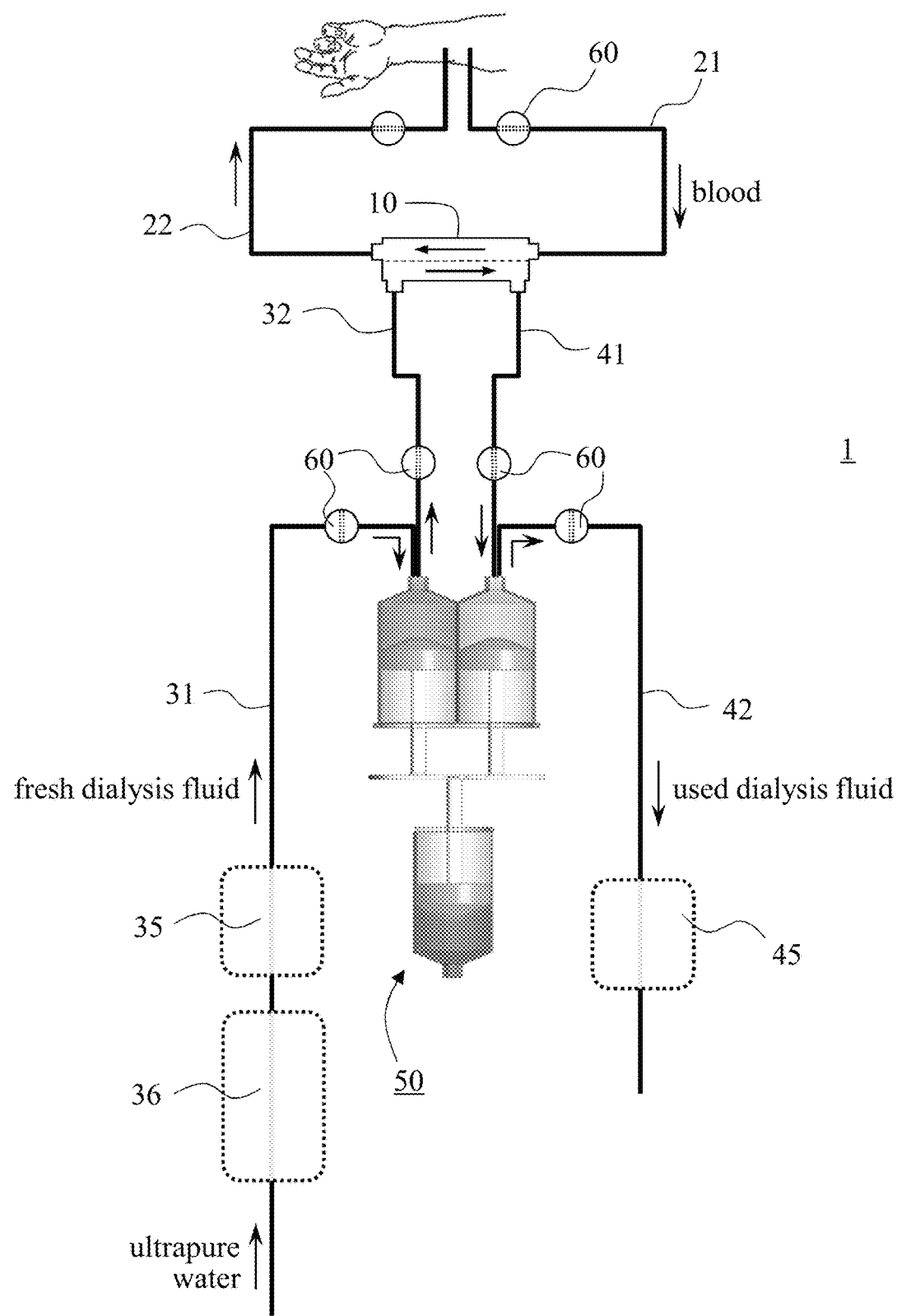
FIG. 23 is a view illustrating a blood purifying apparatus in which a flow controller is configured to control a flow passage through a blood tube, a dialysis fluid supply tube and a dialysis fluid discharge tube.

The blood purifying apparatus 1 according to an embodiment of the present invention may be modified into other structures. For example, the flow controller 60 may be modified such that it can control the flow passages through the supply tube 30, the discharge tube 40, and the blood tube 20. FIG. 23 is a view illustrating the blood purifying apparatus 1 having a flow controller 60 which is configured to control flow passages through the supply tube 30, the discharge tube 40, and the blood tube 20.

Specifically, when the flow controller 60 blocks the first supply tube 31, the first discharge tube 41, and the first blood tube 21, it opens the second supply tube 32, the second discharge tube 42, and the second blood tube 22. When the flow controller 60 opens the first supply tube 31, the first discharge tube 41, and the first blood tube 21, it blocks the second supply tube 32, the second discharge tube 42, and the second blood tube 22. The flow controller 60 may block three tubes while opening the other three tubes, and repeat the blocking and repeating in an alternate manner. In this case, the fluid pumping device 50 may be able to transfer blood without using the blood pump 23.

Figure 24:
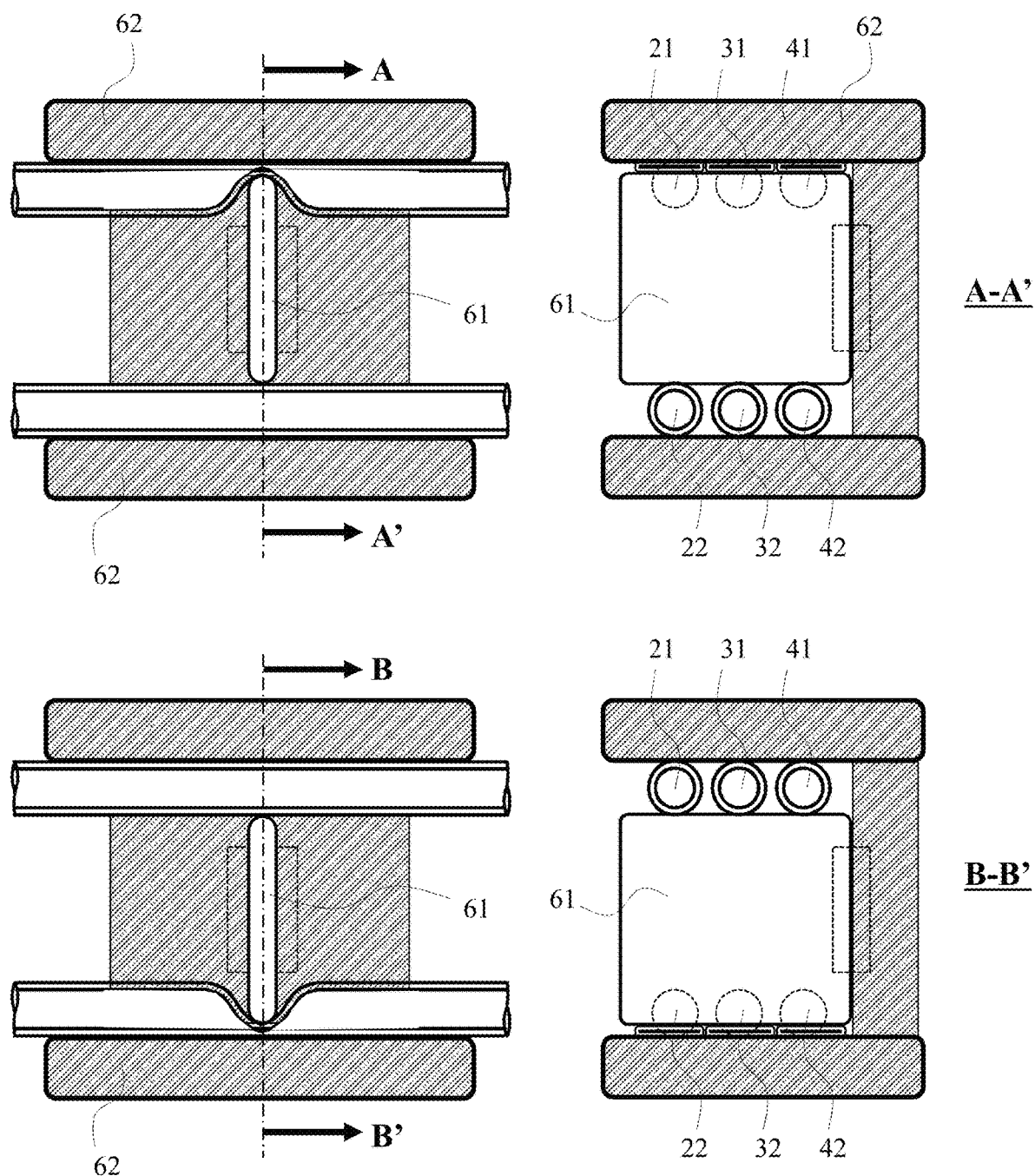
FIGS. 24 to 26 are views illustrating a flow controller of a fluid pumping device according to an embodiment of the present invention.
Figure 25:
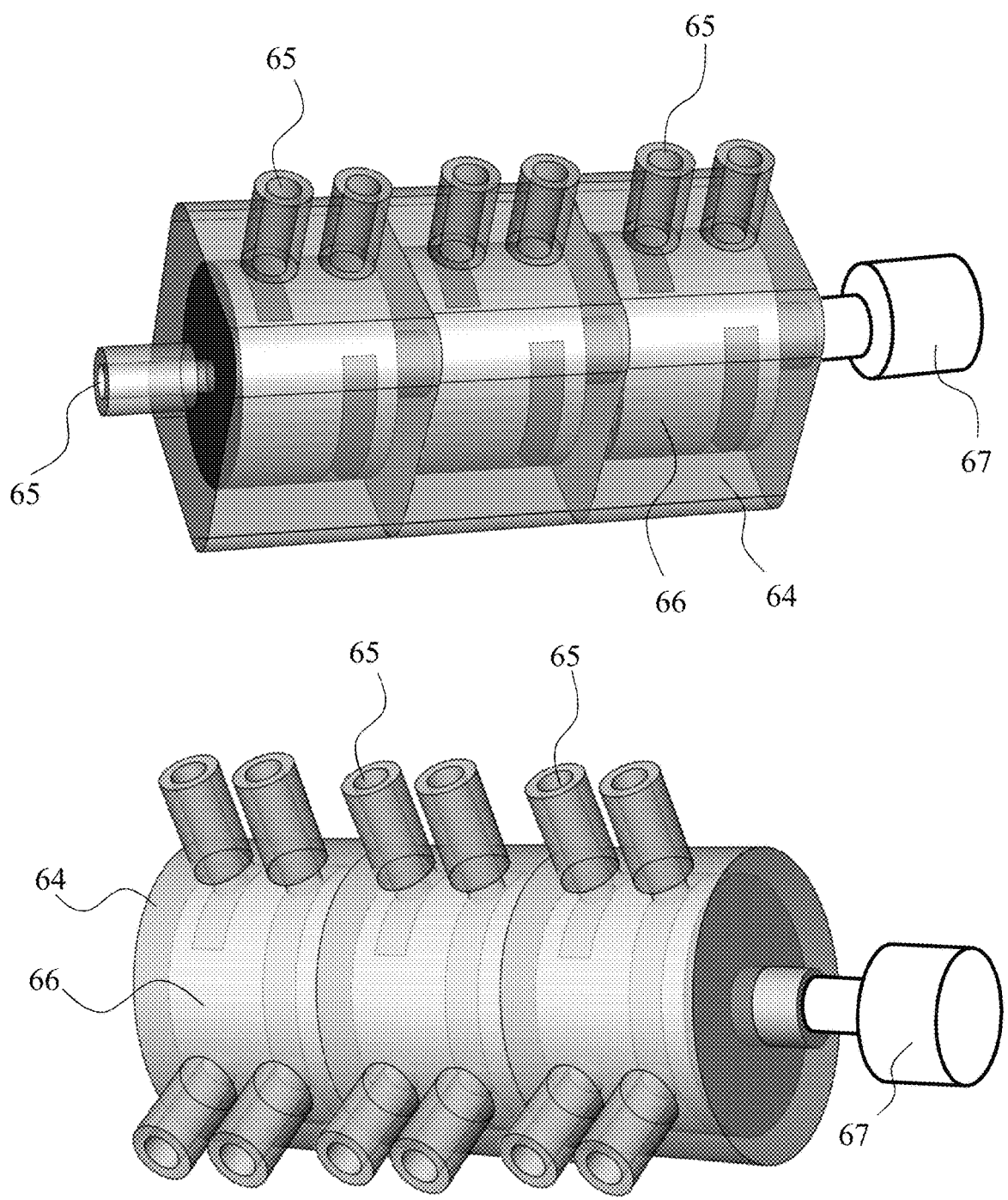
Figure 26:
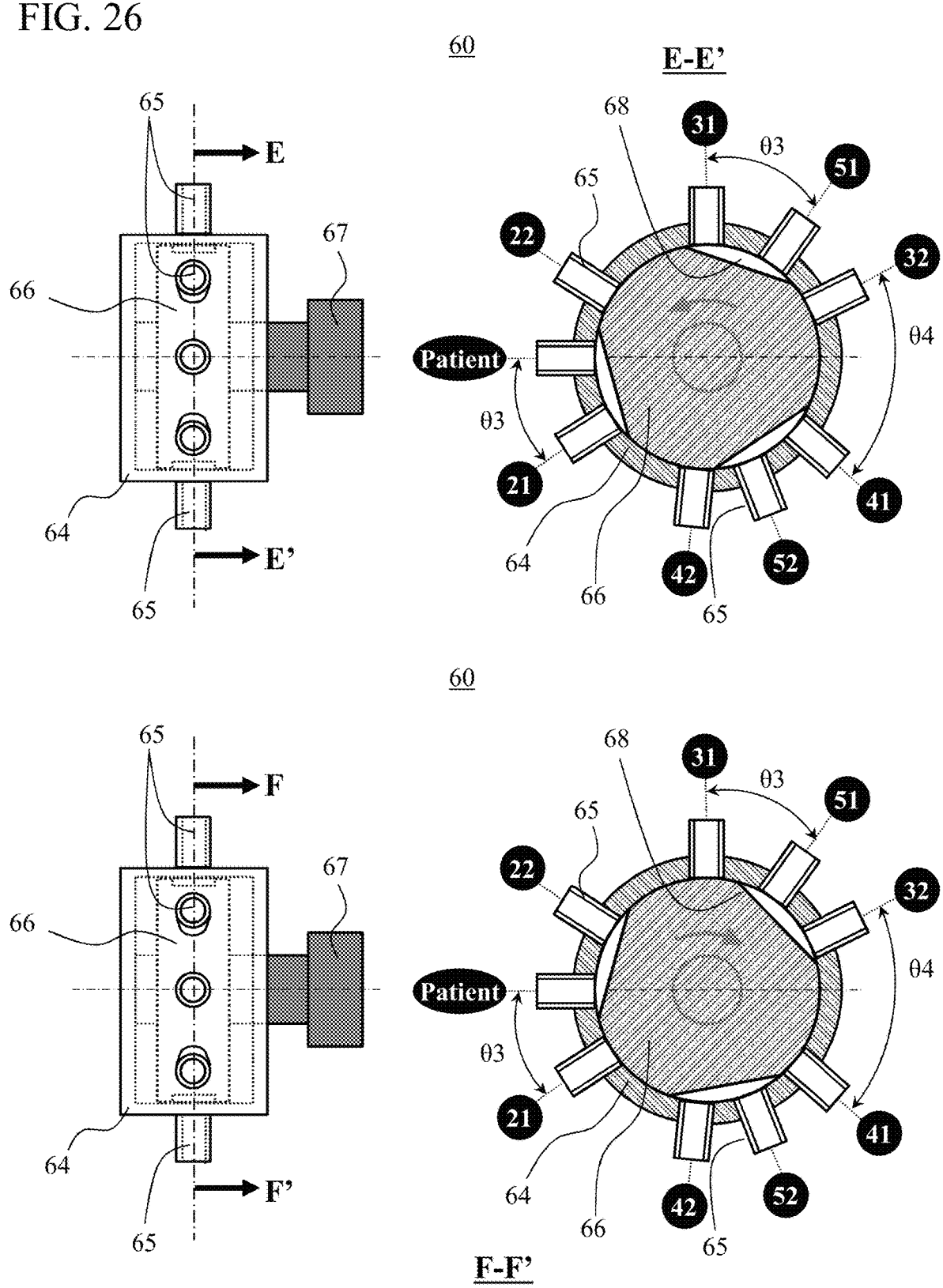

FIGS. 24 to 26 are view illustrating the exemplary flow controllers 60 which can control the flow passage through the supply tube 30, the discharge tube 40, and the blood tube 20. Therefore, the flow-blocking member 61 reciprocating in a straight line may be able to compress the tubes 31, 41 and 21, or the tubes 32, 42, and 22 in an alternate manner. The tubes 31, 41, 21, 32, 42, and 22 are preferably supported by the flow-blocking wall 62. The flow controllers 60 shown in FIGS. 24 to 26 have substantially the same structure as those shown in FIGS. 8 to 10, respectively, and thus, detailed description therefor is avoided. The structure of the flow control device is not limited to that shown in the drawings, and may be modified into other structures that can alternately block the first blood tube 21, the first supply tube 31, and the first discharge tube 41, or the second blood tube 22, the second supply tube 32, and the second discharge tube 42.

Figure 27:
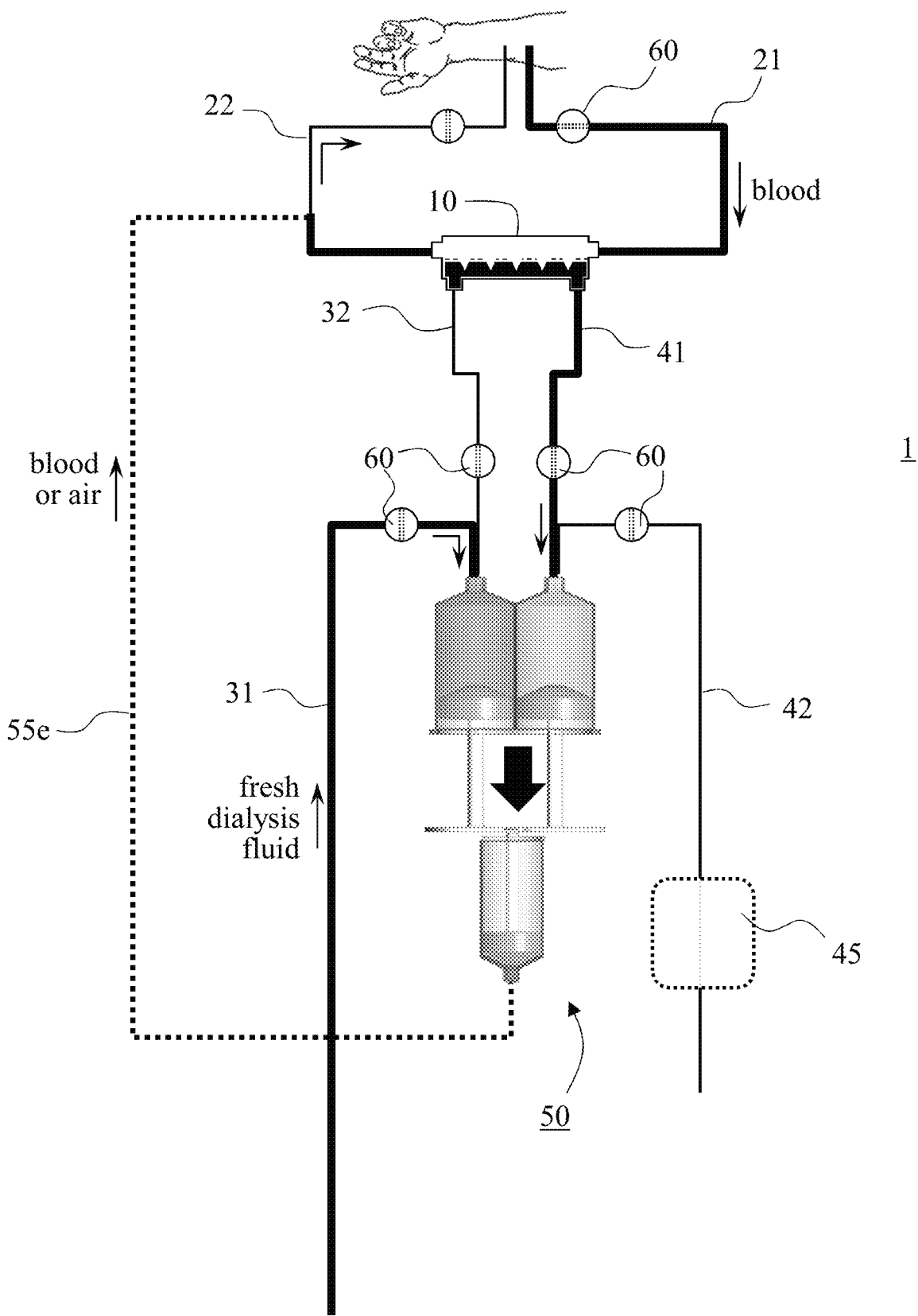
FIGS. 27 and 28 are views illustrating an operation of a fluid pumping device and a blood purifying apparatus according to an embodiment of the present invention.
Figure 28:
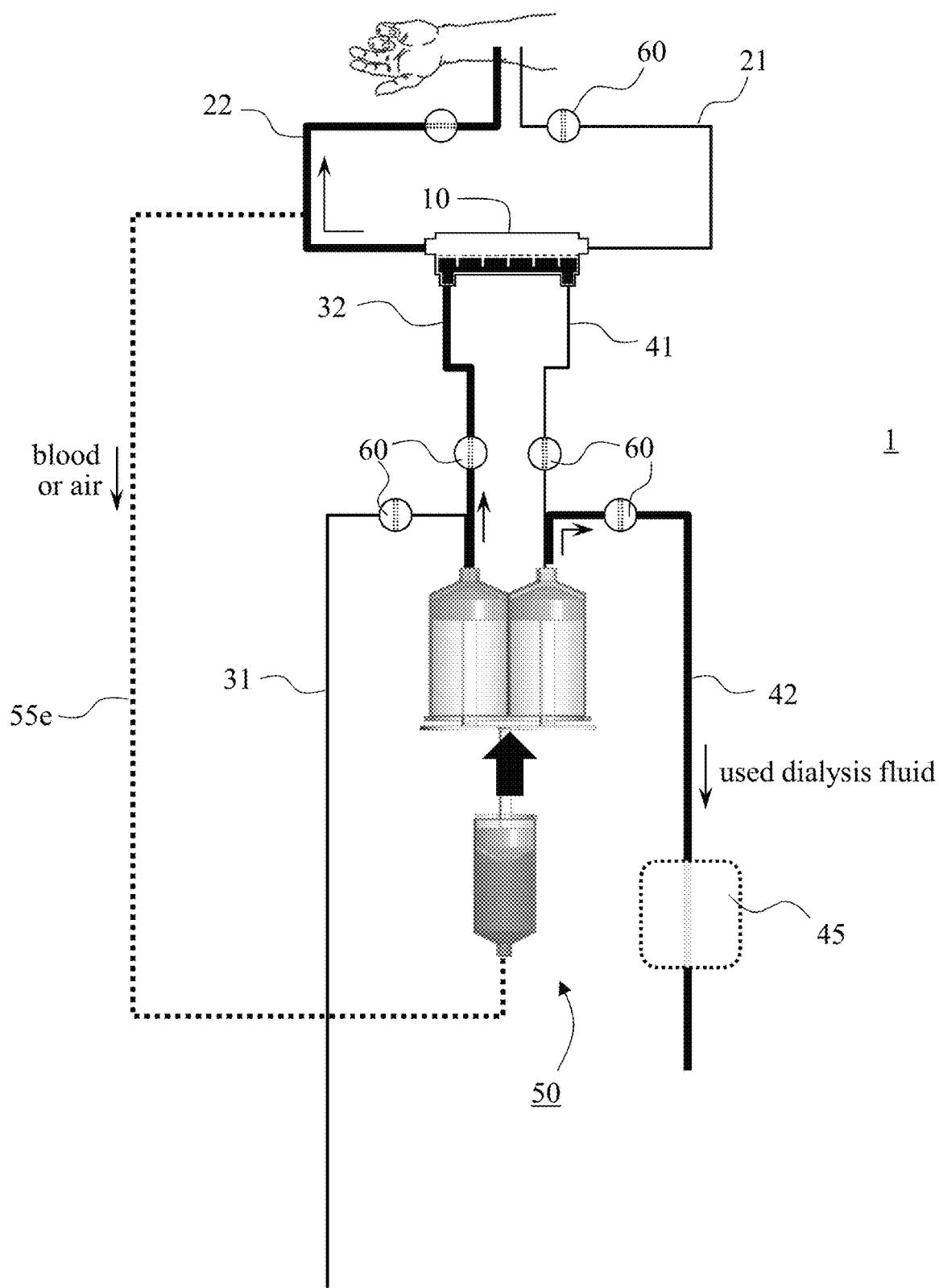
Figure 29:
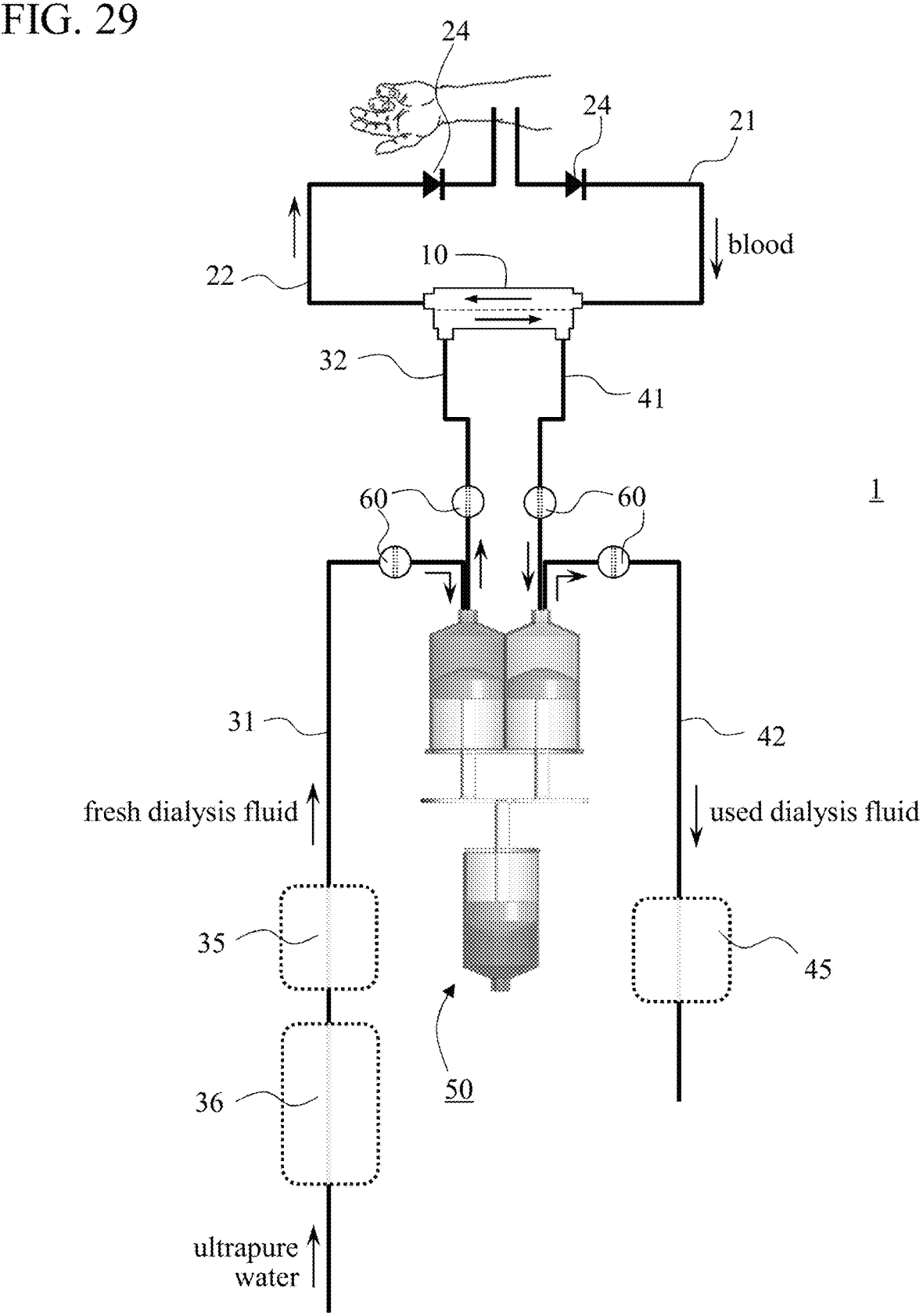
FIG. 29 is a view illustrating a blood purifying apparatus having a one-way valve disposed on a blood tube according to an embodiment of the present invention.

FIGS. 27 and 28 are views illustrating an operation of the blood purifying apparatus 1 according to an embodiment of the present invention.

As shown in FIG. 27, when the first chamber 51 and the second chamber 52 of the fluid pump 50 are expanded and the third chamber 53 is compressed, the flow controller 60 blocks the tubes 32, 42 and 22, and opens the tubes 31, 41 and 21. Due to the expansion of the first chamber 51, fresh dialysis fluid flows into the first chamber 51. Due to the expansion of the second chamber 52, dialysis fluid of the blood purifying filter 10 flows into the second chamber 52. When the dialysis fluid of the blood purifying filter 10 flows into the second chamber 52, since the second supply tube 32 is blocked, the hydraulic pressure of dialysis fluid in the blood purifying filter 10 is lowered below the hydraulic pressure of blood, and filtration occurs. At this time, blood of a patient may be supplied to the blood purifying filter 10 through the first blood tube 21 because the second blood tube 22 is blocked by the flow controller 60. Here, since the third chamber 53 is compressed, blood or air stored in the third chamber 53 may be discharged to the second blood tube 22 and/or to the blood purifying filter 10.

On the other hand, as shown in FIG. 28, when the first chamber 51 and the second chamber 52 of the fluid pump 50 are compressed and the third chamber 53 is expanded, the flow controller 60 opens the tubes 32, 42 and 22, and blocks the tubes 31, 41 and 21. Due to the compression of the second chamber 52, the dialysis fluid of the chamber is discarded therefrom. Due to the compression of the first chamber 51, the dialysis fluid of the chamber is supplied to the blood purifying filter 10. When the dialysis fluid is supplied to the blood purifying filter 10, since the first discharge tube 41 is blocked, the hydraulic pressure of dialysis fluid in the blood purifying filter 10 increases above hydraulic pressures of blood, and backfiltration occurs. At this time, blood of the blood purifying filter 10 may be returned back to a patient through the second blood tube 22 because the first blood tube 21 is blocked by the flow controller 60. Here, since the third chamber 53 is expanded, a portion of blood or air flowing through the second blood tube 22 may flow into the third chamber 53.

As stated above, the flow controller 60 according to an embodiment of the present invention may have a form of a solenoid valve, a rotary valve, an on-off valve, a one-way check valve, and the like. FIG. 28 is an exemplary view illustrating the blood purifying apparatus 1 in which a one-way valve 24 is placed in the blood tube 20 to control the blood flow therethrough.

In addition, the fluid pump 50 according to an embodiment of the present invention is not limited to the aforementioned structure, and may be modified into other structures. FIG. 30 is a view illustrating another exemplary fluid pump 50 according to an embodiment of the present invention. The chambers 51 to 53 may be replaced with fluid sacs 51 to 53 formed of a flexible material that can contract and expand, and the chamber pressurizing member 54 may be replaced with a sac pressurizing member 54 which compresses or expands the sacs 51 to 53. Also, a sac pressurizing member driver (not shown) providing reciprocating movement force to the sac pressurizing member 54 may replace the chamber pressurizing member driver. The sac pressurizing member driver may have various structures that can apply reciprocating movement force to the sac pressurizing member.

Specifically, the sac pressurizing member may compress or expand the first sac and the second sac at the same time while rectilinearly moving along a guide rail disposed on a side wall. In addition, when the first and second sacs are compressed, thereby discharging fluid therein, the third sac may be expanded by the sac pressurizing member to accommodate fluid, and when the first and second sacs are expanded, the third sac may be compressed by the sac pressurizing member. Here, the first sac may be connected to the first supply tube 31 and the second supply tube 32, and the second sac 55 may be connected to the first discharge tube 41 and the second discharge tube 42. Also, the third sac may be connected to either the second blood tube 22 or the first blood tube 21, or both.

Figure 31:
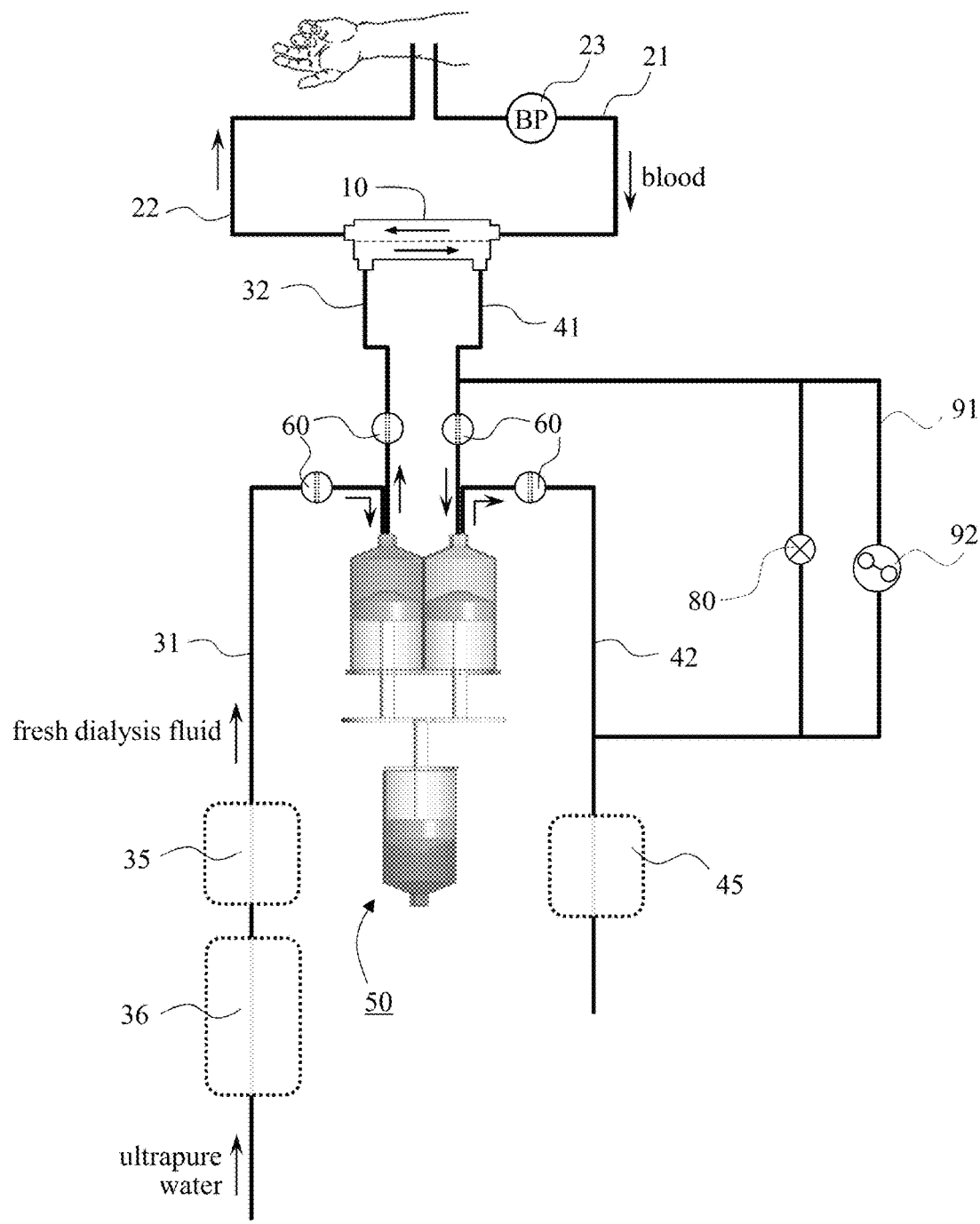
FIG. 31 is a view illustrating a blood purifying apparatus having a pressure relief bypass, an auxiliary discharge tube and an auxiliary dialysis fluid pump according to an embodiment of the present invention.

As stated above, the compression and expansion of the fluid pump 50 configures a cycle of filtration and backfiltration. In the blood purifying treatment using the blood purifying apparatus 1 according to embodiments of the present invention, the cycle of filtration and backfiltration is continuously repeated, removing water and waste products during the filtration and supplementing lost water during the backfiltration. That is, the dialysis fluid pressure increases when the first chamber 51 and the second chamber 52 are compressed whereas it decreases when the first chamber 51 and the second chamber 52 are expanded. When the dialysis fluid pressures fluctuate, the blood purifying apparatus 1 according to an embodiment of the present invention may further include a pressure-relief bypass 80 which connects between the first and second discharge tube 41 and 42. FIG. 31 illustrate the blood purifying apparatus 1 having the pressure-relief bypass 80.

Figure 32:
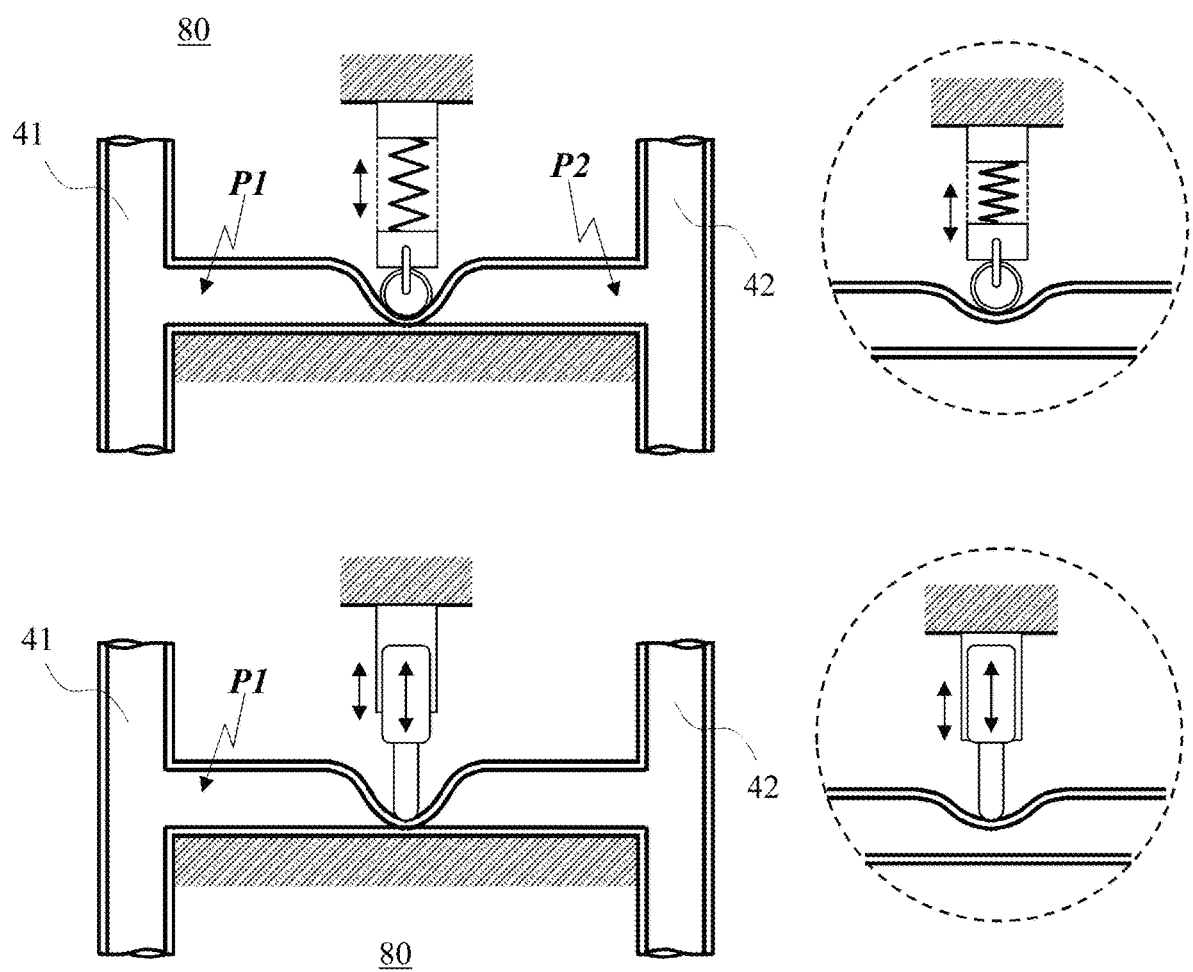
FIG. 32 is a view illustrating a pressure relief bypass according to an embodiment of the present invention.

An exemplary pressure-relief bypass is illustrated in FIG. 32. Under the normal operation, the pressure relief bypass 80 remains closed. However, the dialysis fluid pressure of the blood purifying filter 10 (or the dialysis fluid pressure at the second supply tube 32 or at the first discharge tube 41) exceeds a predetermined value, the pressure-relief bypass opens. The pressure-relief bypass 80 is not limited to be opened or closed by the dialysis fluid pressure of the blood purifying filter 10. The pressure-relief bypass can be opened or closed by the pressure of the second supply tube 32, the pressure difference of the both tubes connected by the pressure-relief bypass 80, or the transmembrane pressure (TMP) of the blood purifying filter 10.

In addition, the blood purifying apparatus 1 according to embodiments of the present invention may additionally be provided with an auxiliary discharge tube 91 connecting between the first discharge tube 41 and the second discharge tube 42, and an auxiliary discharge pump 92 disposed on the auxiliary discharge tube 91 to additionally remove dialysis fluid from the blood purifying filter 10. In a situation where the amounts of dialysis fluid supplied to and discharged from the blood purifying filter 10 are maintained substantially equal to each other due to the operations of the balancing chamber 90, the auxiliary discharge pump 92 may be able to remove water out of blood, thereby removing excess water accumulated in the body of a patient.

The blood purifying apparatus 1 in which the novel fluid pumping device 50 is employed can quickly change the hydraulic pressure of the dialysis fluid inside the blood purifying filter 10. As a result, water exchange and mass transfer between blood and dialysis fluid inside the blood purifying filter 10 can be increased during blood purifying treatment, thereby improving blood purifying efficiency without increasing the size of the blood purifying filter 10 or the flow rates of blood or dialysis fluid. In addition, according to an embodiment of the present invention, blood is transferred without using a mechanical blood pump, the blood purifying apparatus 1 may be further miniaturized and lightened, which is suitable for home hemodialysis or portable hemodialysis.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A fluid pumping device supplying or discharging dialysis fluid, the fluid pumping device comprising:
   a plurality of chambers each having an internal space;
   a chamber pressurizing member compressing or expanding the internal spaces of the plurality of chambers;
   a chamber pressurizing member driver driving the chamber pressurizing member, and
   a flow controller controlling a flow passage, wherein
   the plurality of chambers comprises a first chamber, a second chamber, and a third chamber,
   the first chamber is connected with a first chamber tube through which a dialysis fluid is supplied to the first chamber and a second chamber tube through which a dialysis fluid is removed from the first chamber,
   the second chamber is connected with a third chamber tube through which a dialysis fluid is supplied to the second chamber and a fourth chamber tube through which a dialysis fluid is removed from the second chamber, and
   the third chamber is connected to a fifth chamber tube through which a fluid is supplied to and removed from the third chamber,
   wherein the flow controller controls a flow passage through the first to fourth chamber tubes.

2. The fluid pumping device of claim 1, wherein
   the first chamber and the second chamber are compressed or expanded simultaneously,
   wherein the third chamber is expanded when the first chamber and the second chamber are compressed, and the third chamber is compressed when the first chamber and the second chamber are expanded.

3. The fluid pumping device of claim 2, wherein the chambers are compressed or expanded, the flow controller blocks a flow passage through any two of the first to fourth chamber tubes and opens a flow passage through the other two of the first to fourth chamber tubes.

4. The fluid pumping device of claim 3, wherein the flow controller comprises:
   a flow-blocking member pressurizing the first chamber tube, the second chamber tube, the third chamber tube, or the fourth chamber tube to thereby block a flow passage therethrough;
   a flow-blocking wall supporting the chamber tubes pressurized by the flow-blocking member; and
   a flow-blocking member driver driving the flow-blocking member.

5. The fluid pumping device of claim 3, wherein the flow controller comprises:
   a flow control housing having an internal space with a cylindrical shape;

a flow control rotor having a cylindrical shape and rotatably disposed inside the internal space of the flow control housing;
a plurality of flow control ports, each penetrating the flow control housing; and
a rotor driver driving the flow control rotor, wherein
the flow control rotor blocks a flow passage through at least one of the flow control ports.

6. The fluid pumping device of claim 5, wherein the flow control ports are spaced apart along a circumferential direction of the flow control rotor,
wherein an end of each of the flow control ports placed at an inner surface of the flow control housing is configured to face a cylindrical surface of the flow control rotor.

7. The fluid pumping device of claim 6, wherein the flow control rotor is provided with a recessed portion to facilitate a fluid flow through the flow control ports.

8. A blood purifying apparatus comprising:
a blood purifying filter in which mass transfer occurs between blood and dialysis fluid;
a blood tube connecting between the blood purifying filter and a patient and allowing blood of a patient to flow therethrough;
a blood pump disposed on the blood tube to transfer blood; and
a fluid pumping device according to claim 1.

9. The blood purifying apparatus of claim 8, wherein the first chamber and the second chamber are compressed or expanded simultaneously by the chamber pressurizing member,
the third chamber is expanded when the first chamber and the second chamber are compressed and the third chamber is compressed when the first chamber and the second chamber are expanded, and
when the chambers are compressed or expanded, the flow controller blocks a flow passage through any two of the first to fourth chamber tubes and opens a flow passage through the other two of the first to fourth chamber tubes.

10. The blood purifying apparatus of claim 9, further comprising:
a dialysis fluid supply tube through which dialysis fluid is supplied to the blood purifying filter;
a dialysis fluid discharge tube through which dialysis fluid of the blood purifying filter is discharged;
a first dialysis fluid pump disposed on the dialysis fluid supply tube to supply dialysis fluid to the blood purifying filter; and
a second dialysis fluid pump disposed on the dialysis fluid discharge tube to discharge dialysis fluid of the blood purifying filter, wherein
the dialysis fluid supply tube includes a first supply tube through which dialysis fluid is supplied to the first dialysis fluid pump and a second supply tube connecting between the first dialysis fluid pump and the blood purifying filter and allowing dialysis fluid to be supplied to the blood purifying filter therethrough,
wherein the dialysis fluid discharge tube includes a first discharge tube through which dialysis fluid of the blood purifying filter is discharged to the second dialysis fluid pump and a second discharge tube through which dialysis fluid is discarded therefrom.

11. The blood purifying apparatus of claim 10, wherein the first chamber tube is connected to the first supply tube, the second chamber tube is connected to the second supply tube,
the third chamber tube is connected to the first discharge tube, and
the fourth chamber tube is connected to the second discharge tube.

12. The blood purifying apparatus of claim 10, further comprising a balancing chamber being connected to the second supply tube and second discharge tube, the balancing chamber configured to maintain a difference between an amount of dialysis fluid supplied to the blood purifying filter and an amount of dialysis fluid discharged from the blood purifying filter within a predetermined range, wherein
the second supply tube further includes an upstream second supply tube connecting the first dialysis fluid pump and the balancing chamber and a downstream second supply tube connecting the balancing chamber and the blood purifying filter, and
the second discharge tube further includes an upstream second discharge tube connecting the second dialysis fluid pump and the balancing chamber and the downstream second discharge tube through which dialysis fluid is discarded therefrom,
wherein the second chamber tube is connected to the downstream second supply tube 32b and the fourth chamber tube is connected to the downstream second discharge tube 42b.

13. The blood purifying apparatus of claim 10, wherein the flow controller comprises:
a flow-blocking member pressurizing the first chamber tube, the second chamber tube, the third chamber tube, or the fourth chamber tube to thereby block a flow passage therethrough;
a flow-blocking wall supporting the chamber tubes pressurized by the flow-blocking member; and
a flow-blocking member driver driving the flow-blocking member.

14. The blood purifying apparatus of claim 10, wherein the flow controller comprises:
a flow control housing having an internal space with a cylindrical shape;
a flow control rotor having a cylindrical shape and rotatably disposed inside the internal space of the flow control housing;
a plurality of flow control ports, each penetrating the flow control housing; and
a rotor driver driving the flow control rotor, wherein
the flow control rotor blocks a flow passage through at least one of the flow control ports.

15. The blood purifying apparatus of claim 14, wherein the flow control ports are spaced apart along a circumferential direction of the flow control rotor,
wherein an end of each of the flow control ports placed at an inner surface of the flow control housing is configured to face a cylindrical surface of the flow control rotor.

16. The blood purifying apparatus of claim 14, wherein the flow control rotor is provided with a recessed portion to facilitate a fluid flow through the flow control ports.

17. The blood purifying apparatus of claim 14, wherein the blood tube comprises a first blood tube through which blood of a patient is supplied to the blood purifying filter and a second blood tube through which blood of the blood purifying filter is returned to a patient,
wherein the blood pump is replaced by one-way valves each disposed on the first blood tube and the second blood tube.

* * * * *